United States Patent [19]
Brendel et al.

[11] Patent Number: 5,955,607
[45] Date of Patent: Sep. 21, 1999

[54] SULFONAMIDE-SUBSTITUTED CHROMANS, PROCESSES FOR THEIR PREPARATION, THEIR USE AS A MEDICAMENT OR DIAGNOSTIC, AND PHARMACEUTICAL PREPARATIONS COMPRISING THEM

[75] Inventors: Joachim Brendel, Bad Vilbel; Uwe Gerlach, Hattersheim; Hans Jochen Lang, Hofheim; Klaus Weidmann, Kronberg, all of Germany

[73] Assignee: Hoechst Marion Roussel Deutschland, Germany

[21] Appl. No.: 09/160,304

[22] Filed: Sep. 25, 1998

[30] Foreign Application Priority Data

Sep. 26, 1997 [DE] Germany .......................... 197 42 509

[51] Int. Cl.[6] .................. A61K 31/35; A61K 31/535; C07D 311/68; C07D 413/12
[52] U.S. Cl. ................. 544/151; 514/233.5; 514/456; 540/502; 544/331; 544/376; 544/405; 546/282.7; 546/196; 548/159; 548/214; 548/245; 548/265.6; 548/305.1; 548/311.4; 548/364.4; 549/404
[58] Field of Search .................. 544/151; 546/282.7; 549/404; 514/456

[56] References Cited

U.S. PATENT DOCUMENTS 4,882,353  11/1989  Niewöhner .

FOREIGN PATENT DOCUMENTS

| 2205477 | of 0000 | Canada . |
| 22229947 | of 0000 | Canada . |
| 0 315 009 | 5/1989 | European Pat. Off. . |
| 0 389 861 | 10/1990 | European Pat. Off. . |
| 0 807 629 | 11/1997 | European Pat. Off. . |
| 0 860 440 | 8/1998 | European Pat. Off. . |
| 95/14470 | 6/1995 | WIPO . |

OTHER PUBLICATIONS

Suessbrich, H. et al., "Specific blockade of slowly activating $I_{sK}$ channels by chromanols—impact on the role of $I_{sK}$ channels in epithelia", FEBS Letters 396 (1996), pp. 271–275.

Lohrmann, E. et al., "A new class of inhibitors of cAMP–mediated C1 secretion in rabbit colon, acting by the reduction of cAMP–activated $K^+$conductance", Pflügers Arch—Eur. J. Physiol. 429 (1995), pp. 517–530.

Primary Examiner—Robert W. Ramsuer
Attorney, Agent, or Firm—Finnegan, Henderson, Farabow, Garrett & Dunner, L.L.P.

[57] ABSTRACT

Compounds of the formula I

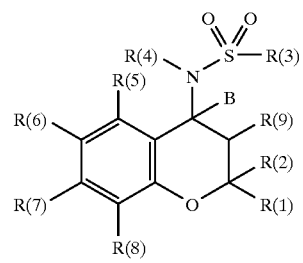

I having the meanings of the substituents indicated in the claims are outstandingly efficacious substances for producing medicaments for the prophylaxis and for the therapy of cardiovascular disorders, in particular arrhythmias, for the treatment of ulcers of the gastrointestinal region or for the treatment of diarrheal disorders.

20 Claims, No Drawings

SULFONAMIDE-SUBSTITUTED CHROMANS, PROCESSES FOR THEIR PREPARATION, THEIR USE AS A MEDICAMENT OR DIAGNOSTIC, AND PHARMACEUTICAL PREPARATIONS COMPRISING THEM

This case claim the benefit under 35 U.S.C. ☐ 119 of German priority document 19742509.7, filed Sep. 26, 1997, which is hereby incorporated by reference.

BACKGROUND OF THE INVENTION

Field of the Invention

The invention relates to compounds of the formula I

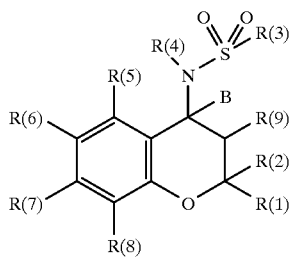

I in which R(1), R(2), R(3), R(4), R(5), R(6), R(7), R(8), R(9), and B have the meanings indicated below, their preparation and their use, in particular in pharmaceuticals. The compounds affect the potassium channel opened by cyclic adenosine monophosphate (cAMP) or the $I_{Ks}$ channel and are outstandingly suitable as pharmaceutical active compounds, for example for the prophylaxis and therapy of cardiovascular disorders, in particular arrhythmias, for the treatment of ulcers of the gastrointestinal area or for the treatment of diarrheal disorders.

In pharmaceutical chemistry, in recent years the 4-acylaminochroman derivatives class has been worked on intensively. The most prominent representative of this class is cromakalim of the formula A (J. Med. Chem. 1986, 29, 2194).

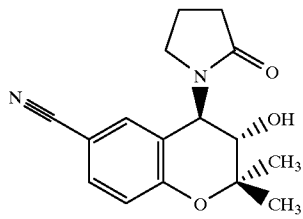

A

Cromakalim and other related 4-acylaminochroman derivatives are compounds having a relaxant action on smooth muscular organs, so they are used for lowering raised blood pressure as a result of vascular muscle relaxation and in the treatment of asthma as a result of relaxation of the smooth musculature of the airways. It is common to all these preparations that they act at the cellular level, for example, of smooth muscle cells and result there in an opening of certain ATP-sensitive $K^+$ channels. The increase in negative charge in the cell (hyperpolarization) induced by the efflux of $K^+$ ions counteracts the increase in the intracellular $Ca^{2+}$ concentration via secondary mechanisms and thus cell activation, which leads, for example, to muscle contraction.

The compounds of the formula I according to the invention differ from these acylamino derivatives structurally, inter alia, by the replacement of the acylamino group by a sulfonylamino function. While cromakalim (formula A) and analogous acylamino compounds act as openers of ATP-sensitive $K^+$ channels, the compounds of the formula I according to the invention having the sulfonylamino structure, however, do not show any opening action on this $K^+$ (ATP) channel, but surprisingly show a strong and specific blocking (closing) action on a $K^+$ channel which is opened by cyclic adenosine monophosphate (cAMP) and differs fundamentally from the $K^+$ (ATP) channel mentioned. More recent investigations show that this $K^+$ (cAMP) channel identified in colonic tissue is very similar, perhaps even identical, to the $I_{Ks}$ channel identified in the cardiac muscles. In fact, it was possible for the compounds of the formula I according to the invention to show a strong blocking action on the $I_{Ks}$ channel in guinea-pig cardiomyocytes and also on the $I_{sK}$ channel expressed in *Xenopus* oocytes. As a result of this blocking of the $K^+$ (cAMP) channel or of the $I_{Ks}$ channel, the compounds according to the invention display pharmacological actions of high therapeutic utility in the living body.

Apart from the abovementioned cromakalim or acylaminochroman derivatives, compounds having a 4-sulfonylaminochroman structure, which, however, differ markedly from the compounds of the formula I according to the invention both in the structure and in the biological action, are also described in the literature. Thus EP-A-315 009 describes chroman derivates having a 4-phenylsulfonylamino structure, which are distinguished by antithrombotic and antiallergic properties. EP-A-389 861 and JP 01294677 describe 3-hydroxychroman or chromene derivatives having a cyclic 4-sulfonylamino group (e.g., compound B), which should act as antihypertensives via activation of the $K^+$ (ATP) channels. EP-A-370 901 describes 3-hydroxychroman or chromene derivatives having a 4-sulfonylamino group, the remaining valency of the N atom bearing a hydrogen atom, which have CNS actions. Further, 4-sulfonylaminochroman derivatives are described in Bioorg. Med. Chem. Lett. 4 (1994), 769–773: "N-sulfonamides of benzopyran-related potassium channel openers: conversion of glyburyde insensitive smooth muscle relaxants to potent smooth muscle contractors" and in FEBS Letters 396 (1996), 271–275: "Specific blockade of slowly activating $I_{sK}$ channels by chromanols . . . " and Pflügers Arch.—Eur. J. Physiol. 429 (1995), 517–530: "A new class of inhibitors of cAMP-mediated $Cl^-$ secretion in rabbit colon, acting by the reduction of cAMP-activated $K^+$ conductance".

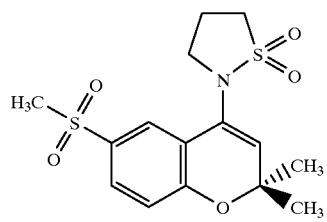

B

The present invention relates to compounds of the formula I

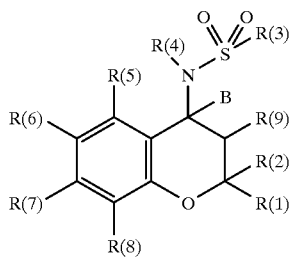

in which:

R(1) and R(2)
  independently of one another are hydrogen, $CF_3$, $C_2F_5$, $C_3F_7$, alkyl having 1, 2, 3, 4, 5, or 6 carbon atoms, or phenyl,
    where phenyl is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, and methylsulfonylamino; or
R(1) and R(2) together are an alkylene chain having 2, 3, 4, 5, 6, 7, 8, 9, or 10 carbon atoms;
R(3) is R(10)—$C_nH_{2n}$—NR(11)— or R(10)—$C_nH_{2n}$—, where one $CH_2$ group in the groups $C_nH_{2n}$ can be replaced by —O—, —CO—, —S—, —SO—, —$SO_2$—, or —NR(12a)—;
  R(12a) is hydrogen, methyl, or ethyl;
  R(10) is hydrogen, methyl, cycloalkyl having 3, 4, 5, 6, 7, or 8 carbon atoms, $CF_3$, $C_2F_5$, or $C_3F_7$;
  n is zero, 1, 2, 3, 4, 5, 6, 7, 8, 9, or 10;
  R(11) is hydrogen or alkyl having 1, 2, 3, 4, 5, or 6 carbon atoms; or
  R(10) and R(11) together are a bond, provided n is not smaller than 3;
R(4) is R(13)—$C_rH_{2r}$—Z—$C_qH_{2q}$—;
  q is 0, 1, 2, 3, 4, 5, 6, 7, or 8;
  r is 0, 1, 2, 3, 4, 5, 6, 7, or 8;
  Z is —CO—NR(14)—,
    —OCO—NR(14)—,
    —O—$C_xH_{2x}$—O—,
    —O—$C_xH_{2x}$—NR(14)—,
    —O—$C_xH_{2x}$—CO—,
    —CO—O—$C_xH_{2x}$—O— or
    —CO—O—$C_xH_{2x}$—NR(14)—,
      where Z may be linked in the forward or reverse directions.
    x is 2, 3, or 4;
  R(14) is hydrogen, alkyl having 1, 2, or 3 carbon atoms,
    —$C_yH_{2y}$—OR(12b), —$C_yH_{2y}$—NR(12b)$_2$;
  R(12b) is hydrogen, methyl, or ethyl;
  y is 2 or 3;
  R(13) is H, $CF_3$, $C_2F_5$, $C_3F_7$, cycloalkyl having 3, 4, 5, 6, 7, or 8 carbon atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;
  R(15) and R(16)
    independently of one another are hydrogen, alkyl having 1,2,3, or 4 carbon atoms or —$C_zH_{2z}$-phenyl,
    z is zero, 1, or 2;
      where phenyl is unsubstituted or substituted by 1 or 2 substituents which are F, Cl, Br, $CF_3$, $NO_2$, CN, OH, methyl, ethyl, methoxy, dimethylamino, sulfamoyl, methylsulfonyl, aminosulfonyl, and methylsulfonylamino; or
  R(15) and R(16)
    together are a chain of 4 or 5 methylene groups, of which one $CH_2$ group can be replaced by —O—, —S—, —NH—, —N($CH_3$)—, or —N(benzyl)—;
  R(17) is hydrogen or alkyl having 1, 2, or 3 carbon atoms;
R(5), R(6), R(7), and R(8)
  independently of one another are hydrogen, F, Cl, Br, I, alkyl having 1, 2, 3, 4, or 5 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —Y—$C_sH_{2s}$—R(18), or phenyl,
    where phenyl is unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
  Y is —O—, —CO—, —CO—O—, —O—CO—, —S—, —SO—, —$SO_2$—, —$SO_2$—O—, —$SO_2$NR(10c), —NR(10c)—, or —CONR(10c)—;
    R(10c) is hydrogen or alkyl having 1, 2, or 3 carbon atoms;
  s is zero, 1, 2, 3, 4, 5, or 6;
  R(18) is hydrogen, $CF_3$, $C_2F_5$, $C_3F_7$, cycloalkyl having 3, 4, 5, 6, 7, or 8 carbon atoms, —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
    where pyridyl, thienyl, imidazolyl, quinolyl, isoquinolyl, and phenyl are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
  R(21) is hydrogen or alkyl having 1, 2, or 3 carbon atoms;
R(9) is hydrogen, OR(10d), or OCOR(10d);
R(10d) is hydrogen or alkyl having 1, 2, or 3 carbon atoms;
B is hydrogen; or
R(9) and B
  together are a bond;
and their physiologically tolerable salts.
Preferred compounds of the formula I are those in which:
R(1) and R(2)
  independently of one another are hydrogen, $CF_3$ or alkyl having 1, 2, 3, 4, 5, or 6 carbon atoms; or
R(1) and R(2) together are an alkylene chain having 2, 3, 4, 5, or 6 carbon atoms;
R(3) is R(10)—$C_nH_{2n}$—;
  R(10) is methyl, $CF_3$ or $C_2F_5$;
  n is zero, 1, or 2;
R(4) is R(13)—$C_rH_{2r}$—Z—$C_qH_{2q}$—;
  q is 1, 2, 3, 4, 5, 6, 7, or 8;

r is 0, 1, 2, 3, 4, 5, 6, 7, or 8;
Z is —CO—NR(14)—,
—OCO—NR(14)—,
—O—$C_xH_{2x}$—O—,
—O—$C_xH_{2x}$—NR(14)—,
—O—$C_xH_{2x}$—CO—O,
—CO—O—$C_xH_{2x}$—O— or
—CO—O—$C_xH_{2x}$—NR(14)—,
  where Z may be linked in the forward or reverse directions;
  x is 2, 3, or 4;
R(14) is hydrogen, alkyl having 1, 2, or 3 carbon atoms, $C_yH_{2y}$—OR(12b), —$C_yH_{2y}$—NR(12b)$_2$;
  R(12b) is hydrogen, methyl, or ethyl;
  y is 2 or 3;
R(13) is H, $CF_3$, $C_2F_5$, $C_3F_7$, cycloalkyl having 3, 4, 5, 6, 7, or 8 carbon atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;
R(15) and R(16)
  independently of one another are hydrogen, alkyl having 1, 2, 3, or 4 carbon atoms or —$C_zH_{2z}$-phenyl,
  z is zero, 1, or 2;
  where phenyl is unsubstituted or substituted by 1 or 2 substituents which are F, Cl, Br, $CF_3$, $NO_2$, CN, OH, methyl, ethyl, methoxy, dimethylamino, sulfamoyl, methylsulfonyl, aminosulfonyl, and methylsulfonylamino; or
R(15) and R(16)
  together are a chain of 4 or 5 methylene groups, of which one $CH_2$ group can be replaced by —O—, —S—, —NH—, —N($CH_3$)—, or —N(benzyl)—;
R(17) is hydrogen or alkyl having 1, 2, or 3 carbon atoms;
R(5), R(6), R(7), and R(8)
  independently of one another are hydrogen, F, Cl, Br, I, alkyl having 1, 2, 3, 4, or 5 carbon atoms, cycloalkyl having 3, 4, 5, 6, or 7 carbon atoms, —CN, —$CF_3$, —$C_2F_5$, —$C_3F_7$, —$NO_2$, —Y— $C_sH_{2s}$—R(18), or phenyl, when phenyl is unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
  Y is —O—, —CO—, —CO—O—, —O—CO—, —S—, —SO—, —$SO_2$—, —$SO_2$—O—, —$SO_2$NR(10c), —NR(10c)—, or —CONR(10c)—;
    R(10c) is hydrogen or alkyl having 1, 2, or 3 carbon atoms;
  s is zero, 1, 2, 3, 4, 5, or 6;
  R(18) is hydrogen, $CF_3$, $C_2F_5$, $C_3F_7$, cycloalkyl having 3, 4, 5, 6, or 7 carbon atoms, —COOR(21), 1-piperidyl, 1-pyrrolidinyl, 4-morpholinyl, 4-methylpiperazin-1-yl, pyridyl, imidazolyl, or phenyl, where pyridyl, imidazolyl, and phenyl are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
    R(21) is hydrogen or alkyl having 1, 2, or 3 carbon atoms;
  R(9) is hydrogen or OR(10d);
    R(10d) is hydrogen or methyl;
  B is hydrogen; or
  R(9) and B
    together are a bond;
and their physiologically tolerable salts.
Particularly preferred compounds of the formula I are those in which:
R(1) and R(2) independently of one another are hydrogen, $CF_3$, or alkyl having 1, 2, or 3 carbon atoms; or
R(1) and R(2) together are an alkylene chain having 2, 3, 4, or 5 carbon atoms;
R(3) is R(10)—$C_nH_{2n}$—;
  R(10) is methyl, $CF_3$, or $C_2F_5$;
  n is zero, 1, or 2;
R(4) is R($^{13}$)—$C_rH_{2r}$—Z—$C_qH_{2q}$—;
  q is 1, 2, 3, or 4;
  r is 0, 1, 2, or 3;
  Z is —CO—NR(14)—,
    —OCO—NR(14)—,
    —O—$C_xH_{2x}$—O—,
    —O—$C_xH_{2x}$—NR(14)—,
    —O—$C_xH_{2x}$—CO—O,
    —CO—O—$C_xH_{2x}$—O— or
    —CO—O—$C_xH_{2x}$—NR(14)—,
    where Z may be linked in the forward or reverse directions;
    x is 2 or 3;
  R(14) is hydrogen, alkyl having 1 or 2 carbon atoms;
  R(13) is $CH_3$, $CF_3$, $C_2F_5$, cycloalkyl having 3, 4, 5, 6, or 7 carbon atoms, —NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;
  R(15) and R(16)
    independently of one another are hydrogen or alkyl having 1, 2, 3, or 4 carbon atoms; or
  R(15) and R(16)
    together are a chain of 4 or 5 methylene groups, of which one $CH_2$ group can be replaced by —O—, —S—, —NH—, —N($CH_3$)—, or —N(benzyl)—;
  R(17) is hydrogen or alkyl having 1 or 2 carbon atoms;
R(5) and R(6)
  independently of one another are hydrogen, F, Cl, Br, alkyl having 1, 2, 3, 4, or 5 carbon atoms, cycloalkyl having 3, 4, 5, 6, or 7 carbon atoms, —CN, —$CF_3$, —$C_2F_5$, —$NO_2$, —Y—$C_sH_{2s}$— R(18), or phenyl, where phenyl is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;
  Y is —O—, —CO—, —$SO_2$—, or —CONR(10c)—;
    R(10c) is hydrogen or alkyl having 1 or 2 carbon atoms;
  s is zero, 1, 2, 3, 4, 5, or 6;

R(18) is hydrogen, $CF_3$, $C_2F_5$, cycloalkyl having 3, 4, 5, 6, or 7 carbon atoms, 1-piperidyl, 1-pyrrolidinyl, 4-morpholinyl, 4-methylpiperazin-1-yl, pyridyl, imidazolyl, or phenyl, where pyridyl, imidazolyl, and phenyl are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, and methylsulfonylamino;

R(7) and R(8)
are hydrogen;

R(9) is hydrogen or OR(10d);
R(10d) is hydrogen or methyl;

B is hydrogen; or

R(9) and B
together form a bond;

and their physiologically tolerable salts.

Very particularly preferred compounds of the formula I are those in which:

R(1) and R(2) are methyl;
R(3) is methyl or ethyl;
R(4) is R(13)—$C_rH_{2r}$—Z—$C_qH_{2q}$—;
q is 1, 2, 3, or 4;
r is 0, 1, 2, or 3;
Z is —CO—NR(14)—,
—OCO—NR(14)—,
—O—$C_xH_{2x}$—NR(14)— or
—CO—O—$C_xH_{2x}$—NR(14)—;
x is 2 or 3;
R(14) is hydrogen or methyl;
R(13) is $CH_3$, $CF_3$, —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —$CF_3$, —Y—$C_sH_{2s}$—R(18), or phenyl,
where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;

Y is —O—, —CO—, or —CONR(10c)—;
R(10c) is hydrogen or methyl;
s is 1, 2, 3, 4, or 5;
R(18) is hydrogen, $CF_3$, or phenyl,
where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, and methylsulfonylamino;

R(7) and R(8) are hydrogen;
R(9) is hydrogen;
B is hydrogen;
and their physiologically tolerable salts.

Very particularly preferred compounds of the formula I are also those in which:
R(1) and R(2) are methyl;
R(3) is methyl or ethyl;

R(4) is R(13)—$C_rH_{2r}$—Z—$C_qH_{2q}$—;
q is 1, 2, 3, or 4;
r is 0, 1, 2, or 3;
Z is —CO—NR(14)—,
—OCO—NR(14)—,
—O—$C_xH_{2x}$—NR(14)— or
—CO—O—$C_xH_{2x}$—NR(14)—;
x is 2 or 3;
R(14) is hydrogen or methyl;
R(13) is $CH_3$, $CF_3$, —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —$CF_3$, —Y— $C_sH_{2s}$—R(18) or phenyl,
where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, and methylsulfonylamino;

Y is —O—, —CO—, or —CONR(10c)—;
R(10c) is hydrogen or methyl;
s is 1, 2, 3, 4, or 5;
R(18) is hydrogen, $CF_3$, or phenyl,
where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, and methylsulfonylamino;

R(7) and R(8) are hydrogen;
R(9) is OH;
B is hydrogen;
and their physiologically tolerable salts.

Very particularly preferred compounds of the formula I are furthermore those in which:
R(1) and R(2) are methyl;
R(3) is methyl or ethyl;
R(4) is R(13)—$C_rH_{2r}$—Z—$C_qH_{2q}$—;
q is 1, 2, 3, or 4;
r is 0, 1, 2, or 3;
Z is —CO—NR(14)—,
—OCO—NR(14)—,
—O—$C_xH_{2x}$—NR(14)— or
—CO—O—$C_xH_{2x}$—NR(14)—;
x is 2 or 3;
R(14) is hydrogen or methyl;
R(13) is $CH_3$, $CF_3$, —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —$CF_3$, —Y—$C_sH_{2s}$—R(18) or phenyl, where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;

Y is —O—, —CO—, or —CONR(10c)—;

R(10c) is hydrogen or methyl;

s is 1, 2, 3, 4, or 5;

R(18) is hydrogen, $CF_3$, or phenyl, where phenyl is unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, or methylsulfonylamino;

R(7) and R(8) are hydrogen;

R(9) and B together are a bond;

and their physiologically tolerable salts.

Alkyl radicals and alkylene radicals can be straight-chain or branched. This also applies to the alkylene radicals of the formulae $C_rH_{2r}$, $C_qH_{2q}$, $C_nH_{2n}$, and $C_sH_{2s}$. Alkyl radicals and alkylene radicals can also be straight-chain or branched if they are substituted or are contained in other radicals, e.g. in an alkoxy radical or in an alkylmercapto radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, and eicosyl. The divalent radicals derived from these radicals, e.g., methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc., are examples of alkylene radicals.

N-containing heterocycles having 1, 2, 3, 4, 5, 6, 7, 8, or 9 carbon atoms are, in particular, the aromatic systems 1-, 2-, or 3-pyrrolyl, 1-, 2-, 4-, or 5-imidazolyl, 1-, 3-, 4-, or 5-pyrazolyl, 1,2,3-triazol-1-, -4-, or 5-yl, 1,2,4-triazol-1-, -3-, or -5-yl, 1-, or 5-tetrazolyl, 2-, 4-, or 5-oxazolyl, 3-, 4-, or 5-isoxazolyl, 1,2,3-oxadiazol-4-, or 5-yl, 1,2,4-oxadiazol-3-, or -5-yl, 1,3,4-oxadiazol-2-yl, or -5-yl, 2-, 4-, or 5-thiazolyl, 3-, 4-, or 5-isothiazolyl, 1,3,4-thiadiazol-2-, or -5-yl, 1,2,4-thiadiazol-3- or -5-yl, 1,2,3-thiadiazol-4-, or -5-yl, 2-, 3-, or 4-pyridyl, 2-, 4-, 5-, or 6-pyrimidinyl, 3- or 4-pyridazinyl, pyrazinyl, 1-, 2-, 3-, 4-, 5-, 6- or 7-indolyl, 1-, 2-, 4-, or 5-benzimidazolyl, 1-, 3-, 4-, 5-, 6-, or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7-, or 8-cinnolinyl, 2-, 3-, 5-, 6-, 7-, or 8-quinoxalinyl, 1-, 4-, 5-, 6-, 7-, or 8-phthalazinyl.

Particularly preferred N-containing heterocycles are pyrrolyl, imidazolyl, quinolyl, pyrazolyl, pyridyl, pyrazinyl, pyrimidinyl and pyridazinyl.

Thienyl represents both 2- and 3-thienyl.

Monosubstituted phenyl radicals can be substituted in the 2-, 3- or the 4-position, or disubstituted in the 2,3-, 2,4-, 2,5-, 2,6-, 3,4- or 3,5-position. The same also applies correspondingly for the N-containing heterocycles or the thiophene radical.

In the case of disubstitution of a radical the substituents can be identical or different.

If the radicals R(1) and R(2) together are an alkylene chain, these radicals with the carbon atom bearing them form a ring which has one carbon atom in common with the 6-membered ring in the formula I, thus a spiro-compound is then present. If R(9) and B together are a bond, a 2H-chromene parent structure is present. If R(10) and R(11) together are a bond, the group R(10)—$C_nH_{2n}$—NR(11)— preferably is a nitrogen heterocycle bonded via a nitrogen atom. If R(10) and R(11) together are a bond and the group R(10)—$C_nH_{2n}$—NR(11)— is a nitrogen heterocycle bonded via a nitrogen atom, this nitrogen heterocycle is preferably a 4-membered ring or a ring larger than a 4-membered ring, e.g., a 5-membered ring, 6-membered ring, or 7-membered ring.

If the compounds of the formula I contain one or more acidic or basic groups or one or more basic heterocycles, the invention also includes the corresponding physiologically or toxicologically tolerable salts, in particular the pharmaceutically utilizable salts. Thus the compounds of the formula I which bear acidic groups, e.g., one or more COOH groups, can be used, for example, as alkali metal salts, preferably sodium or potassium salts, or as alkaline earth metal salts, e.g., calcium or magnesium salts, or as ammonium salts, e.g., as salts with ammonia or organic amines or amino acids. Compounds of the formula I which bear one or more basic, i.e., protonatable, groups or contain one or more basic heterocyclic rings can also be used in the form of their physiologically tolerable acid addition salts with inorganic or organic acids, for example as hydrochlorides, phosphates, sulfates, methanesulfonates, acetates, lactates, maleates, fumarates, malates, gluconates, etc. If the compounds of the formula I simultaneously contain acidic and basic groups in the molecule, the invention also includes internal salts, so-called betaines, in addition to the salt forms described. Salts can be obtained from the compounds of the formula I according to customary processes, for example by combination with an acid or base in a solvent or dispersant or alternatively from other salts by anion exchange.

In the case of appropriate substitution, the compounds of the formula I can be present in stereoisomeric forms. If the compounds of the formula I contain one or more centers of asymmetry, these can independently of one another have the S configuration or the R configuration. The invention includes all possible stereoisomers, e.g., enantiomers or diastereomers, and mixtures of two or more stereoisomeric forms, e.g., enantiomers and/or diastereomers, in any desired ratios. The invention thus relates to enantiomers, for example, in enantiomerically pure form, both as dextro- and as levorotatory antipodes, and also in the form of mixtures of the two enantiomers in different ratios or in the form of racemates. If cis/trans isomerism is present, the invention relates to both the cis form and the trans form and mixtures of these forms. Individual stereoisomers can be prepared, if desired, by resolution of a mixture according to customary methods or, for example, by stereoselective synthesis. If mobile hydrogen atoms are present, the present invention also includes all tautomeric forms of the compounds of the formula I.

The compounds of the formula I can be prepared by different chemical processes, which are likewise included by the present invention. Thus a compound of the formula I, for example, is obtained by a) reacting a compound of the formula II

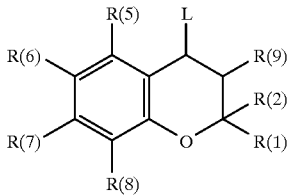

II in which R(1), R(2), R(5), R(6), R(7), R(8), and R(9) have the meanings indicated above and L is a nucleofugic leaving group, in particular Cl, Br, I, methanesulfonyloxy, or p-toluenesulfonyloxy, in a manner known per se with a sulfonamide or its salt of the formula III

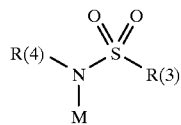

III in which R(3) and R(4) have the meanings indicated above and M is hydrogen or preferably a metal equivalent, particularly preferably lithium, sodium, or potassium; or by b) reacting a compound of the formula IV

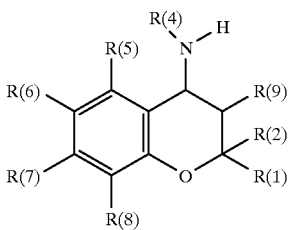

IV in which R(1), R(2), R(4), R(5), R(6), R(7), R(8), and R(9) have the meanings indicated above, with a sulfonic acid derivative of the formula V

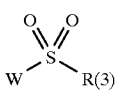

V in which R(3) has the meanings indicated above and W is a nucleofugic leaving group, such as, for example, fluorine, bromine, 1-imidazolyl, but in particular chlorine; or by c) reacting a compound of the formula VI

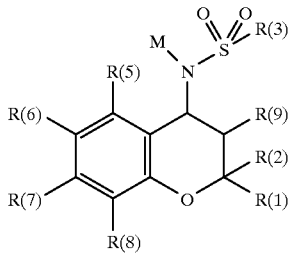

VI in which R(1), R(2), R(3), R(5), R(6), R(7), R(8), R(9) and M have the meanings indicated above, in a manner known per se in the sense of an alkylation reaction with an alkylating agent of the formula VII,

R(4)—L                                     VII in which R(4) and L have the meanings indicated above; or by d) carrying out an electrophilic substitution reaction in a compound of the formula I

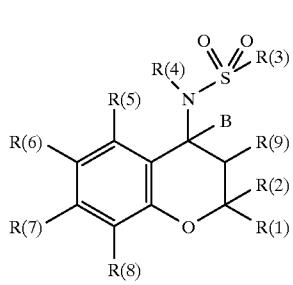

I in which R(1) to R(9) and B have the meanings indicated above, in at least one of the positions R(5), R(6), R(7), and R(8), if this position is hydrogen; or by e) reacting a compound of the formula VIII

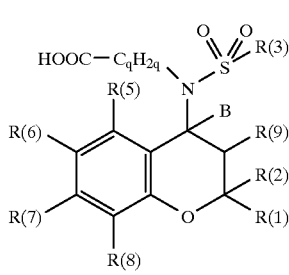

VIII in which R(1), R(2), R(3), R(5), R(6), R(7), R(8), R(9), q, and B have the meanings indicated above, with a compound of the formula IX, X or XI, $R(13) - C_rH_{2r} - NHR(14)$     IX $R(13) - C_rH_{2r} - O - C_xH_{2x} - OH$     X -continued

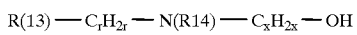

in which R(13), R(14), r and x have the meanings indicated above, in the sense of an esterification or amidation reaction; or by f) reacting a compound of the formula XII

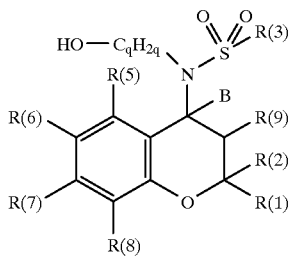

in which R(1), R(2), R(3), R(5), R(6), R(7), R(8), R(9), q, and B have the meanings indicated above, with a compound of the formula XIII or XIV

in which R(13), R(14), r, x and L have the meanings indicated above, in the sense of an alkylation reaction; or by g) reacting a compound of the formula XV,

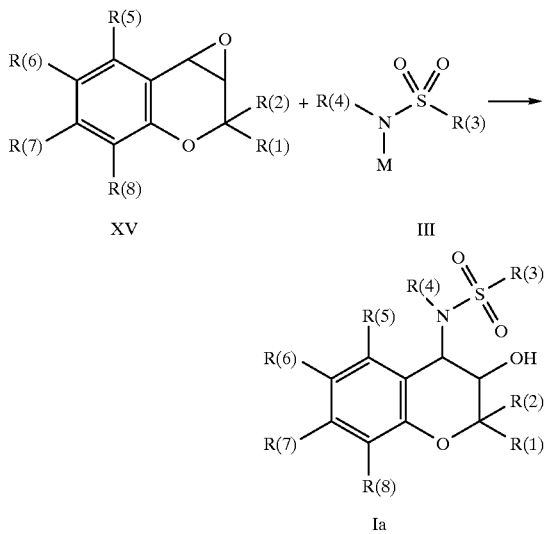

in which R(1), R(2), R(5), R(6), R(7), and R(8) have the meanings indicated above, with a sulfonamide of the formula III in which R(3), R(4) and M have the meanings indicated above or M is advantageously also a trialkylsilyl radical, e.g., a trimethylsilyl radical, to give a chromanol of the formula Ia; or by h) converting a compound of the formula Ia,

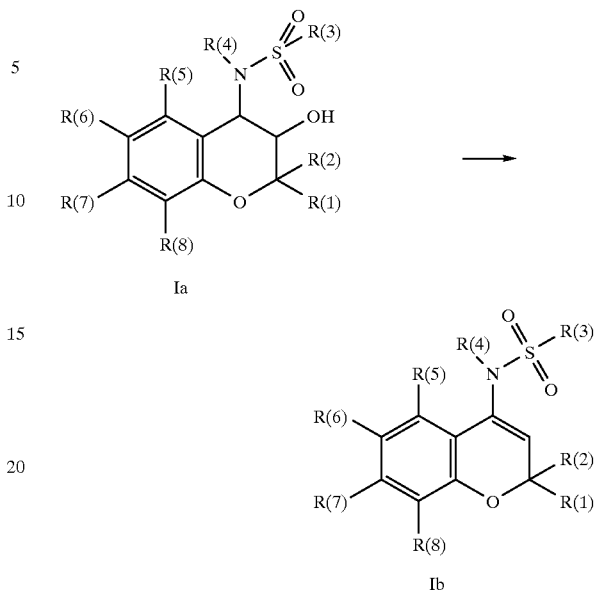

in which R(1) to R(8) have the meanings indicated above, in the sense of an elimination reaction to give a compound of the formula Ib, in which R(1) to R(8) have the meanings indicated above.

Procedure a) corresponds to the nucleophilic substitution of a leaving group in a reactive bicyclic system of the formula II by a sulfonamide or one of its salts of the formula III. Because of the higher nucleophilicity and higher reactivity of a sulfonamide present in the salt form, when using a free sulfonamide (formula III, M=H), it is preferred to first generate a sulfonamide salt (formula III, M=metal cation) from this by action of a base. If a free sulfonamide (formula III, M=H) is employed, the deprotonation of the sulfonamide to the salt can be carried out in situ. Preferably, those bases are used which are not alkylated or only slightly alkylated themselves, such as, for example, sodium carbonate, potassium carbonate, sterically strongly hindered amines, e.g., dicyclohexylamine, N,N-dicyclohexylethylamine, or other strong nitrogen bases having low nucleophilicity, for example DBU (diazabicycloundecene), N,N',N'''-triisopropylguanidine etc. However, other customarily used bases can also be employed for the reaction, such as potassium tert-butoxide, sodium methoxide, alkali metal hydrogencarbonates, alkali metal hydroxides, such as, for example, LiOH, NaOH or KOH, or alkaline earth metal hydroxides, such as, for example, $Ca(OH)_2$.

The reaction is preferably carried out in a solvent, particularly preferably in polar organic solvents such as, for example, dimethylformamide (DMF), dimethylacetamide (DMA), dimethyl sulfoxide (DMSO), tetramethylurea, (TMU), hexamethylphosphoramide (HMPA), tetrahydrofuran (THF), dimethoxyethane (DME) or other ethers, or, for example, also in a hydrocarbon such as toluene or in a halogenated hydrocarbon such as chloroform or methylene chloride etc. It is also possible to carry out the reaction, however, in polar protic solvents, such as, for example, in water, methanol, ethanol, isopropanol, ethylene glycol or its oligomers and their corresponding hemiethers or alternatively their ethers. The reaction can also be carried out in mixtures of these solvents. It is likewise also possible to carry out the reaction, however, without solvent. The reaction is preferably carried out in a temperature range from −10° C. to +140° C., particularly preferably in a range from 20° C. to 100° C. Conveniently, procedure a) can also be carried out under the conditions of a phase-transfer catalysis.

The compounds of the formula II are obtained according to methods known from the literature, for example from the corresponding alcohols (formula II, L=—OH) by action of hydrogen halide HL (L=Cl, Br, I) or by action of an inorganic acid halide (POCl$_3$, PCl$_3$, PCl$_5$, SOCl$_2$, SOBr$_2$) or by free-radical halogenation of the corresponding chroman derivatives (formula II, L=H) with elemental chlorine or bromine, or with free-radical-activatable halogenating agents such as N-bromosuccinimide (NBS) or SO$_2$Cl$_2$ (sulfuryl chloride) in the presence of a radical chain initiator such as energy-rich light of the visible or ultraviolet wavelength range or by use of a chemical free-radical initiator such as azodiisobutyronitrile.

Procedure b)

describes the reaction, which is known per se and frequently used, of a reactive sulfonyl compound of the formula V, in particular of a chlorosulfonyl compound (W=Cl), with an amino derivative of the formula IV to give the corresponding sulfonamide derivative of the formula I. In principle, the reaction can be carried out without solvent, but reactions of this type are in most cases carried out using a solvent.

The reaction is preferably conducted using a polar solvent, preferably in the presence of a base, which can itself be advantageously used as a solvent, e.g., when using triethylamine, in particular pyridine and its homologs. Solvents likewise used are, for example, water, aliphatic alcohols, e.g., methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPA. The reaction is in this case carried out at a temperature from 0° C. to 160° C., preferably from 20° C. to 100° C.

The amines of the formula IV are obtained in a manner known from the literature, preferably from the corresponding carbonyl compounds of the formula XVI

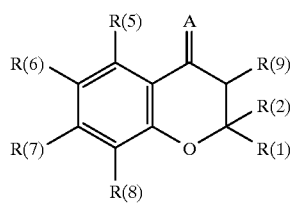

XVI in which R(1), R(2), R(5), R(6), R(7), R(8), and R(9) have the meanings indicated above and A is oxygen, either with ammonia or an amine of the formula XVII,

R(4)—NH$_2$      XVII in which R(4) has the meanings indicated, under reductive conditions or reductive catalytic conditions, preferably at relatively elevated temperature and in an autoclave. In this reaction, primarily by condensation reaction of the ketones of the formula XVI (A=oxygen) and the amines of the formula XVII in situ, Schiff bases of the formula XVI in which A is R(4)—N═ are formed which can be converted immediately, i.e. without prior isolation, into the amines of the formula IV by reduction. However, it is also possible to prepare the Schiff bases (formula XVI, A is R(4)—N═) intermediately formed in the condensation reaction from the compounds of the formulae XVI and XVII according to methods known from the literature and to first isolate them, in order to then convert them in a separate step using a suitable reductant, such as, for example, NaBH$_4$, LiAlH$_4$, NaBH$_3$CN, or by catalytic hydrogenation in the presence of, for example, Raney nickel or a noble metal such as, for example, palladium, into the compounds of the formula IV.

The compounds of the formula IV in which R(4) is hydrogen can advantageously also be obtained in a manner known from the literature by reduction of oximes or oxime ethers (formula XVI, A is ═N—OR, R=H or alkyl) or hydrazones (formula XVI, A is ═N—NR$_2$, R is, for example, ═H or alkyl), e.g., using a complex metal hydride or by catalytic hydrogenation. The oximes and hydrazones necessary for this are preferably prepared in a manner known per se from the ketones of the formula XVI (A=oxygen) using hyrdazine or one of its derivatives or, for example, using hydroxylamine hydrochloride under dehydrating conditions. Particularly advantageously, the compounds of the formula IV in which R(4) is hydrogen can also be obtained by amination using a suitable ammonium compound, e.g., ammonium acetate, in the presence of a suitable reductant, such as, for example, NaCNBH$_3$, (J. Am. Chem. Soc. 93, 1971, 2897).

Alternatively, the amino derivatives of the formula IV can also be obtained in a manner known per se from the literature by reaction of the reactive compounds of the formula II where R(1), R(2), R(5), R(6), R(7), R(8), R(9), and L have the meaning indicated, either with ammonia or an amine of the formula XVII where R(4) has the meaning indicated.

Procedure c)

represents the alkylation reaction, which is known per se, of a sulfonamide or of one of its salts VI with an alkylating agent of the formula VII. Corresponding to the analogy of the reaction to procedure a), the reaction conditions already described in detail under procedure a) apply to procedure c). In addition to the bases already mentioned there, sodium hydride or a phosphazene base are preferably used for the deprotonation of the sulfonamide.

The preparation of the sulfonamide derivatives VI (where M=H) and their precursors has already been described in procedure b), where R(4) is then in each case hydrogen. The preparation of the alkylating agent VII is carried out by analogous literature procedures or as described under procedure a), preferably from the corresponding hydroxy compounds (formula VII where L is —OH).

Procedure d)

describes the further chemical conversion of compounds of the formula I according to the invention into other compounds of the formula I by electrophilic substitution reactions in one or more of the positions designated by R(5) to R(8), which in each case are hydrogen.

Preferred substitution reactions are 1. aromatic nitration to introduce one or more nitro groups, some or all of which can be reduced to amino groups in subsequent reactions. The amino groups can in turn be converted into other groups in subsequent reactions, for example in a Sandmeyer reaction, e.g., to introduce cyano groups;
2. aromatic halogenation, in particular to introduce chlorine, bromine or iodine;
3. chlorosulfonation, e.g., by action of chlorosulfonic acid to introduce a chlorosulfonyl group, which can be converted into other groups in subsequent reactions, e.g., into a sulfonamide group;

4. the Friedel-Crafts acylation reaction to introduce an acyl radical or a sulfonyl radical by action of the corresponding acid chlorides in the presence of a Lewis acid as a Friedel-Crafts catalyst, preferably in the presence of anhydrous aluminum chloride.

Procedure e)

describes the esterification of carboxylic acids of the formula VIII with alcohols of the formula X or XI or amidation with amines of the formula IX. Numerous methods have been described in the literature for these reactions. These reactions can be carried out particularly advantageously by activation of the carboxylic acid, e.g., using dicyclohexylcarbodiimide (DCC), if appropriate with addition of hydroxybenzotriazole (HOBT) or dimethylaminopyridine (DMAP), or using O-[(cyano(ethoxycarbonyl)-methylen)amino]-1,1,3,3-tetramethyluronium tetrafluoroborate (TOTU). However, reactive acid derivatives can also be synthesized first according to known methods, e.g., acid chlorides by reaction of the carboxylic acids of the formula VIII with inorganic acid halides, such as, for example, $SOCl_2$, or acid imidazolides by reaction with carbonyldiimidazole, which are then subsequently reacted, if appropriate with addition of an auxiliary base, with the alcohols or amines of the formula IX, X or XI.

The carboxylic acids of the formula VIII are obtained according to the methods described under a) to d), where, however, R(4) is then in each case $—C_qH_{2q}COOH$ or $—C_qH_{2q}COOalkyl$ and in the latter case a subsequent hydrolysis of the ester is additionally carried out.

Procedure f)

describes the alkylation of an alcohol of the formula XII using an alkylating agent of the formula XIII or XIV. For this purpose, the alcohol is first converted by action of a suitable base, such as, for example, sodium hydride or a phosphazene base, into an alcoholate salt which is then reacted with the alkylating agent in a suitable polar solvent, such as, for example, dimethylformamide, at temperatures between 20° C. and 150° C. The deprotonation of the alcohol to the salt can also be carried out in situ, bases then preferably being employed which are not alkylated themselves, such as, for example, potassium carbonate.

The alcohols of the formula XII are obtained according to the methods described under a) to d), where then, however, R(4) is in each case $—C_qH_{2q}OH$ or $—C_qH_{2q}OR$ (R=suitable protective group, e.g. acetoxy) and in the latter case a subsequent removal of the protective group is additionally carried out.

Procedure g)

corresponds to the nucleophilic opening of an epoxide of the formula XV by a sulfonamide or one of its salts of the formula III. The reaction can be carried out under conditions analogous to those described for procedure a). The use of the free sulfonamide in the presence of a substoichiometric amount, e.g., 20–80%, of the corresponding base, e.g. sodium hydride, has proven particularly advantageous. Likewise advantageous is the use of sulfonamide derivatives in which M is a trialkylsilyl radical, e.g. a trimethylsilyl radical, it then being expedient to carry out the reaction in the presence of a fluoride, e.g., tetrabutylammonium fluoride.

The epoxides of the formula XV are obtained according to methods known from the literature from the corresponding olefins of the formula XVIII

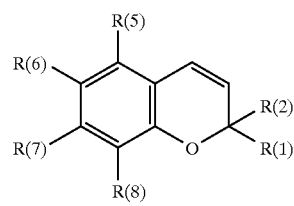

XVIII in which R(1), R(2), R(5), R(6), R(7), and R(8) have the meanings indicated above, e.g., by action of a suitable inorganic or organic peroxide, such as, for example, $H_2O_2$ or m-chloroperbenzoic acid, or by base-catalyzed cyclization of the corresponding bromohydrin, which can be obtained from XVIII, for example, by reaction with N-bromosuccinimide and water. The epoxides of the formula XV can also be obtained from the olefins of the formula XVIII in optically pure form by oxidation in the presence of the chiral Jacobsen catalyst, such as is described, for example, in Tetrahedron Lett. 32, 1991, 5055. The olefins of the formula XVIII can be obtained either from the ketones of the formula XVI (A=oxygen) by reduction of the carbonyl group to an OH function and subsequent acid-catalyzed elimination or by thermal cyclization of suitably substituted aryl propargyl ethers, such as described, for example, in J. Org. Chem. 38 (1973) 3832.

Procedure h)

describes the conversion of a chromanol of the formula Ia into a chromene of the formula Ib by elimination. For this purpose, the chromanol can be subjected to dehydration either directly in the presence of an acid or base or an activation of the hydroxyl group can first be carried out, e.g., by acetylation with acetic anhydride or mesylation with methanesulfonyl chloride, after which a base-catalyzed elimination can subsequently be carried out, e.g. by heating with DBU (diazabicycloundecene).

Apart from the procedures described, a number of other approaches to the compounds of the formula I according to the invention are conceivable. Thus it can be useful, for example, in isolated cases to combine the reactions described under procedures a) to h) with one another in another sequence or, analogously to the methods described, first to prepare compounds not according to the invention in which the radicals R(1) to R(8) have a meaning other than that indicated, and which are then converted into a compound according to the invention in the last stage by a simple conversion of one of the substituents, such as, for example, alkylation, amidation, etc.

In the case of all procedures, it may be appropriate to temporarily protect functional groups in the molecule in certain reaction steps. Such protective group techniques are familiar to the person skilled in the art. The selection of a protective group for groups under consideration and the processes for their introduction and removal are described in the literature and can be adapted to the individual case, if appropriate, without difficulties.

It has already been said that the compounds of the formula I surprisingly have a strong and specific blocking (closing action) on a $K^+$ channel which is opened by cyclic adenosine monophosphate (cAMP) and fundamentally differs from the well-known $K^+$ (ATP) channel, and that this $K^+$ (cAMP) channel identified in colonic tissue is very similar, perhaps even identical, to the $I_{K_s}$ channel identified in the cardiac muscle. For the compounds according to the invention, it was possible to show a strong blocking action on the $I_{Ks}$ channel in guinea-pig cardiomyocytes and on the $I_{sK}$ channel expressed in *Xenopus oocytes*. As a result of this blocking of the K⁺ (cAMP) channel or the $I_{Ks}$ channel, the compounds according to the invention display pharmacological actions of high therapeutic utility in the living organism and are outstandingly suitable as pharmaceutical active compounds for the therapy and prophylaxis of various syndromes.

Thus the compounds of the formula I according to the invention are distinguished as a novel active compound class of potent inhibitors of stimulated gastric acid secretion. The compounds of the formula I are thus valuable pharmaceutical active compounds for the therapy and prophylaxis of ulcers of the stomach and of the intestinal region, for example of the duodenum. They are likewise suitable on account of their strong gastric secretion-inhibiting action as excellent therapeutics for the therapy and prophylaxis of reflux esophagitis.

The compounds of the formula I according to the invention are furthermore distinguished by an antidiarrheal action and are therefore suitable as pharmaceutical active compounds for the therapy and prophylaxis of diarrheal disorders.

The compounds of the formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially of cardiac arrhythmias which can be eliminated by action potential prolongations. They can be used especially for the therapy and prophylaxis of atrial fibrillation and atrial flutters and also for the therapy and prophylaxis of reentry arrhythmias and for the prevention of sudden cardiac death as a result of ventricular fibrillation.

Although numerous substances having antiarrhythmic activity are already on the market, there is still no compound which is really satisfactory with respect to activity, range of application and side effects profile, so there is furthermore a need for the development of improved antiarrhythmics. The action of numerous known antiarrhythmics of the so-called class III is based on an increase in the myocardial refractory time due to prolongation of the action potential duration. This is essentially determined by the extent of repolarizing K⁺ currents which flow out of the cell via various K⁺ channels. Particularly great importance is ascribed here to the so-called "delayed rectifier" $I_K$, of which two subtypes exist, a rapidly activated $I_{Kr}$ and a slowly activated $I_{Ks}$. Most known class III antiarrhythmics mainly or exclusively block $I_{Kr}$ (e.g. dofetilide, d-sotalol). However, it has been shown that these compounds have an increased proarrhythmic risk at low or normal heart rates, in particular arrhythmias which are designated as "torsades de pointes" being observed (D. M. Roden; "Current Status of Class III Antiarrhythmic Drug Therapy"; Am. J. Cardiol. 72 (1993), 44B–49B). In the case of higher heart rates or stimulation of the β receptors, however, the action potential-prolonging action of the $I_{Kr}$ blockers is markedly reduced, which is attributed to the fact that under these conditions the $I_{Ks}$ contributes more strongly to the repolarization. For these reasons, the substances according to the invention, which act as $I_{Ks}$ blockers, have significant advantages compared with the known $I_{Kr}$ blockers. Meanwhile, it has also been described that a correlation exists between $I_{Ks}$ channel-inhibitory action and the suppression of life-threatening cardiac arrhythmias, such as are induced, for example, by β-adrenergic hyperstimulation (e.g. B. T. J. Colatsky, C. H. Follmer and C. F. Starmer; "Channel Specificity in Antiarrhythmic Drug Action; Mechanism of potassium channel block and its role in suppressing and aggravating cardiac arrhythmias"; Circulation 82 (1990), 2235–2242; A. E. Busch, K. Malloy, W. J. Groh, M. D. Varnum, J. P. Adelman and J. Maylie; "The novel class III antiarrhythmics NE-10064 and NE-10133 inhibit $I_{sK}$ channels in *Xenopus oocytes* and $I_{Ks}$ in guinea pig cardiac myocytes"; Biochem. Biophys. Res. Commun. 202 (1994),265–270).

Moreover, the compounds contribute to a marked improvement of cardiac insufficiency, in particular of congestive heart failure, advantageously in combination with contraction-promoting (positively inotropic) active substances, e.g., phosphodiesterase inhibitors.

In spite of the therapeutically useful advantages which can be achieved by blockade of the $I_{Ks}$, to date only very few compounds have been described which inhibit this subtype of the "delayed rectifier". The substance azilimide which is in development admittedly has a blocking action on the $I_{Ks}$, but mainly blocks the $I_{Kr}$ (selectivity 1:10). WO-A-95/14470 claims the use of benzodiazepines as selective blockers of the $I_{Ks}$. Further $I_{Ks}$ blockers are described in FEBS Letters 396 (1996), 271–275: "Specific blockade of slowly activating $I_{sK}$ channels by chromanols . . . " and Pflugers Arch.—Eur. J. Physiol. 429 (1995), 517–530: "A new class of inhibitors of cAMP-mediated Cl⁻ secretion in rabbit colon, acting by the reduction of cAMP-activated K⁺ conductance". The potency of the 3-hydroxychromanols mentioned there, however, is lower than that of the compounds of the formula I according to the invention.

The compounds of the formula I according to the invention and their physiologically tolerable salts can thus be used in animals, preferably in mammals, and in particular in man as pharmaceuticals per se, as mixtures with one another or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments having K⁺ channel-blocking action. The present invention furthermore relates to pharmaceutical preparations which, as active constituent, contain an efficacious dose of at least one compound of the formula I and/or of a physiologically tolerable salt thereof in addition to customary, pharmaceutically innocuous excipients and auxiliaries. The pharmaceutical preparations normally contain 0.1 to 90 percent by weight of the compounds of the formula I and/or their physiologically tolerable salts. The production of the pharmaceutical preparations can be carried out in a manner known per se. To this end, the compounds of the formula I and/or their physiologically tolerable salts are brought, together with one or more solid or liquid pharmaceutical excipients and/or auxiliaries and, if desired, in combination with other pharmaceutical active compounds, into a suitable administration form or dose form, which can then be used as a pharmaceutical in human medicine or veterinary medicine.

Pharmaceuticals which contain compounds of the formula I according to the invention and/or their physiologically tolerable salts can be administered orally, parenterally, e.g., intravenously, rectally, by inhalation or topically, the preferred administration being dependent on the individual case, e.g., the particular clinical picture of the disorder to be treated. The person skilled in the art is familiar on the basis of his expert knowledge with the auxiliaries which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solublizers, agents for achieving a depot effect, buffer substances or colorants.

The compounds of the formula I can also be combined with other pharmaceutical active compounds to achieve an advantageous therapeutic action. Thus in the treatment of cardiovascular disorders, advantageous combinations with substances having cardiovascular activity are possible. Possible advantageous combination components of this type which are advantageous for cardiovascular disorders are, for example, other antiarrhythmics, i.e., class I, class II or class III antiarrhythmics, such as, for example, $I_{Kr}$ channel blockers, e.g., dofetilide, or furthermore hypotensive substances such as ACE inhibitors (for example enalapril, captopril, ramipril), angiotensin antagonists, $K^+$ channel activators, and also alpha- and beta-receptor blockers, but also sympathomimetic compounds and compounds having adrenergic activity, as well as $Na^+/H^+$ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with $H_2$ antagonists (e.g., ranitidine, cimetidine, famotidine, etc.), in particular when administered for the treatment of gastrointestinal disorders.

For an oral administration form, the active compounds are mixed with the additives suitable therefor, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, sugar or starch, in particular maize starch. The preparation can take place here both as dry and as moist granules. Suitable oily excipients or solvents are, for example, vegetable or animal oils, such as sunflower oil or codliver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds are brought into solution, suspension or emulsion, if desired with the substances customary for this purpose such as solubilizers, emulsifiers or other auxiliaries. The compounds of the formula I and their physiologically tolerable salts can also be lyophilized and the lyophilizates obtained used, for example, for the preparation of injection or infusion preparations. Suitable solvents are, for example, water, physiological saline solution or alcohols, e.g., ethanol, propanol, glycerol, and in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also contain other pharmaceutical auxiliaries such as surfactants, emulsifiers and stabilizers and also a propellant. Such a preparation customarily contains the active compound in a concentration of approximately 0.1 to 10, in particular of approximately 0.3 to 3, % by weight.

The dose of the active compound of the formula I or of the physiologically tolerable salts thereof to be administered depends on the individual case and is to be adapted to the conditions of the individual case for an optimal action as customary. But it depends, of course, on the frequency of administration and on the potency and duration of action of the compounds in each case employed for therapy or prophylaxis, but also on the nature and severity of the disease to be treated and on the sex, age, weight and individual responsiveness of the human or animal to be treated and on whether the therapy is acute or prophylactic. Customarily, the daily dose of the compound of the formula I in the case of administration to the patient weighing approximately 75 kg is 0.001 mg/kg of body weight to 100 mg/kg of body weight, preferably 0.01 mg/kg of body weight to 20 mg/kg of body weight. The dose can be administered in the form of an individual dose or divided into a number, e.g., two, three or four, individual doses. In particular when treating acute cases of cardiac arrhythmias, for example in an intensive care unit, a parenteral administration by injection or infusion, e.g., by an intravenous continuous infusion, may be advantageous.

Experimental section

LIST OF THE ABBREVIATIONS

| | |
|---|---|
| CDI | Carbonyl diimidazole |
| CONC. | concentrated |
| DCC | dicyclohexylcarbodiimide |
| dil. | dilute |
| DIPE | diisopropyl ether |
| DMA | N,N-dimethylacetamide |
| DMAP | 4-dimethylaminopyridine |
| DMSO | dimethyl sulfoxide |
| EA | ethyl acetate |
| m.p. | melting point |
| HOBT | 1-hydroxy-1H-benzotriazole |
| in vac. | in vacuo. |
| solvt | solvent |
| NaH | sodium hydride; 60 percent dispersion, if not stated otherwise |
| PE | petroleum ether |
| RT | room temperature |
| THF | tetrahydrofuran |
| Phosphazene base P1 | phosphazene base P1-t-Bu-tris-tetramethylene(tert-butyliminotripyrrolidinophosphorane) |

EXAMPLE 1

5-[Ethylsulfonyl-(2,2,6-trimethylchroman-4-yl)amino]pentanamide

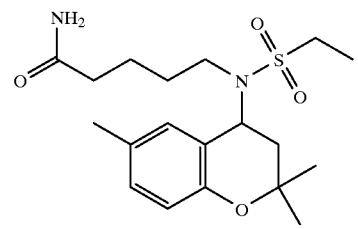

a) A solution of 50 g (0.33 mol) of 2-hydroxy-5-methylacetophenone, 240 ml of acetonitrile, 56.6 g (0.79 mol) of pyrrolidine and 115 g (1.97 mol) of acetone is stirred at RT for 6 days. The reaction mixture is concentrated on a rotary evaporator and the residue is stirred with EA and dil. hydrochloric acid. The organic phase is separated off and washed a further 2 times with dil. hydrochloric acid. After distilling off the solvent, the residue is purified by chromatography using cyclohexane/EA 95:5, and 45 g of 2,2,6-trimethylchroman-4-one are obtained.

b) 28.5 g (0.15 mol) of 2,2,6-trimethylchroman-4-one and 116 g (1.5 mol) of ammonium acetate in 550 ml of methanol are treated with 65.9 g (1.05 mol) of sodium cyanoborohydride, and the mixture is heated to 60° C. for 18 h. After cooling, the batch is acidified cautiously with conc. hydrochloric acid and allowed to stand overnight. It is then poured onto 500 ml of water, rendered alkaline with potash and extracted 2 times using 500 ml of EA each time. After concentration of the organic phases, the residue is adjusted to pH 1.0 with hydrochloric acid and extracted 2 times with EA. The aqueous phase is saturated with potash and extracted 3 times with EA. After drying and concentrating these extracts, 19.4 g of 4-amino-2,2,6-trimethylchroman are obtained.

c) 18.3 g (0.18 mol) of triethylamine and 6.4 g (0.05 mol) of ethanesulfonyl chloride are successively added dropwise with cooling in an ice bath to a solution of 8.7 g (0.045 mol) of 4-amino-2,2,6-trimethylchroman in 130 ml of THF. After stirring overnight at RT, the precipitate is filtered off and the filtrate is concentrated in vacuo. The concentrated filtrate is taken up in EA and washed successively with dil. hydrochloric acid and sodium bicarbonate solution. After drying over magnesium sulfate and concentrating in vacuo, 8.8 g of 4-ethylsulfonylamino-2,2,6-trimethylchroman are obtained.

d) 4.0 g (14.1 mmol) of 4-ethylsulfonylamino-2,2,6-trimethylchroman dissolved in 52 ml of DMF are added dropwise to a suspension of 0.49 g (16.2 mmol) of sodium hydride (80 percent dispersion) in 34 ml of DMF. After stirring at RT for 1 h, 2.75 g (14.1 mmol) of methyl 5-bromovalerate are added and the mixture is stirred overnight at RT. The DMF is then distilled off in vacuo, the residue is shaken with water and ethyl acetate and the organic phase is washed with dil. hydrochloric acid and sodium bicarbonate solution. After drying over magnesium sulfate and concentrating in vacuo, 5.1 g of methyl 5-[ethylsulfonyl-(2,2,6-trimethyl-chroman-4-yl)amino]pentanoate are obtained.

e) A solution of 0.4 g (1 mmol) of methyl 5-[ethylsulfonyl-(2,2,6-trimethyl-chroman-4-yl)amino]pentanoate and 1.5 ml of liquid ammonia in 10 ml of methanol is allowed to stand at RT for 9 days. After concentrating in vacuo, the residue is treated with water and extracted with EA. 0.37 g of 5-[ethylsulfonyl-(2,2,6-trimethylchroman-4-yl)amino]pentanamide is obtained; m.p. 127–129° C.

EXAMPLE 2

5-[Ethylsulfonyl-(2,2,6-trimethylchroman-4-yl)amino]pentanoic acid (2-diethylaminoethyl)amide

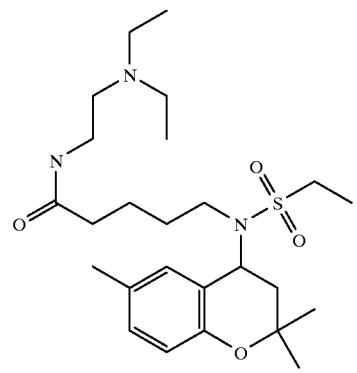

a) 0.5 g (1.25 mmol) of methyl 5-[ethylsulfonyl-(2,2,6-trimethyl-chroman-4-yl)amino]pentanoate (Example 1d) is stirred overnight at RT with 0.21 g (3.77 mmol) of KOH in 20 ml of methanol. After stripping off the solvent in vacuo, the residue is acidified with hydrochloric acid and extracted with EA. 0.4 g of 5-[ethylsulfonyl-(2,2,6-trimethylchroman-4-yl)amino]pentanoic acid is obtained.

b) A solution of 0.3 g (0.78 mmol) of 5-[ethylsulfonyl-(2,2,6-trimethylchroman-4-yl)amino]pentanoic acid, 0.11 g (0.78 mmol) of HOBT and 0.18 g (0.86 mmol) of DCC in 4 ml of DMF is stirred at 0° C. for 1 h. 0.09 g (0.78 mmol) of diethylaminoethylamine is then added and the mixture is stirred overnight at RT. It is treated with 50 ml of water and 50 ml of EA, and the organic phase is washed twice with 25 ml each of saturated sodium bicarbonate solution and additionally twice with water. After drying over magnesium sulfate and concentrating in vacuo, 0.3 g of 5-[ethylsulfonyl-(2,2,6-trimethylchroman-4-yl)amino]pentanoic acid (2-diethylaminoethyl)amide is obtained.

EXAMPLE 3

5-[Ethylsulfonyl-(2,2,6-trimethylchroman-4-yl)amino]pentanoic acid (3-imidazol-1-ylpropyl)amide

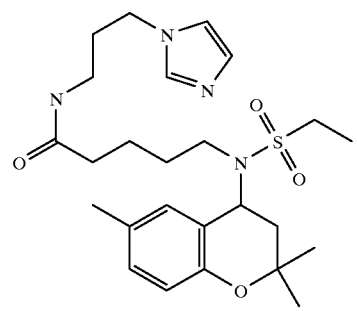

0.32 g of 5-[ethylsulfonyl-(2,2,6-trimethylchroman-4-yl)amino]pentanoic acid (3-imidazol-1-ylpropyl)amide is obtained from 0.28 g of 5-[ethylsulfonyl-(2,2,6-trimethylchroman-4-yl)amino]pentanoic acid (Example 2a), 0.01 g of HOBT, 0.17 g of DCC and 0.092 g of 1-aminopropylimidazole in 10 ml of methylene chloride analogously to Example 2b.

EXAMPLE 4

2-(2-Ethoxyethoxy)ethyl [(2,2-diethyl-6-methylchroman-4-yl)-ethylsulfonylamino]acetate

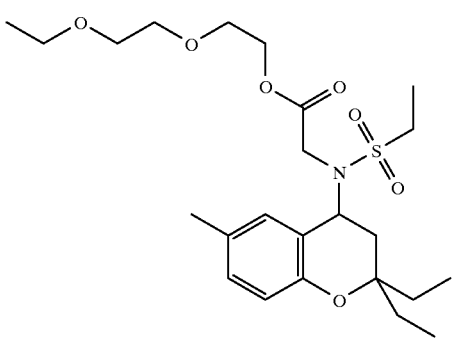

a) A solution of 50 g (0.33 mol) of 2-hydroxy-5-methylacetophenone, 240 ml of acetonitrile, 56.6 g (0.79 mol) of pyrrolidine and 170 g (1.97 mol) of 3-pentanone is stirred at RT for 5 days and then additionally heated to 65° C. for 12 h. The reaction mixture is concentrated on a rotary evaporator and the residue is stirred with EA and dil. hydrochloric acid. The organic phase is separated off and additionally washed twice with dil. hydrochloric acid. After distilling off the solvent, the residue is purified by chromatography using cyclohexane/EA 9:1. To remove 2-hydroxy-5-methylacetophenone which is still present, the product fractions are dissolved in 800 ml of tert-butyl methyl ether and extracted 4 times with 500 ml each of 1M NaOH. After drying and concentrating the organic phase, 28 g of 2,2-diethyl-6-methylchroman-4-one are obtained.

b) By reductive amination of 21.8 g of 2,2-diethyl-6-methylchroman-4-one with ammonium acetate and sodium cyanoborohydride as described in Example 1 b, 21.5 g of 4-amino-2,2-diethyl-6-methylchroman are obtained.

c) 11.7 g of 2,2-diethyl-4-ethylsulfonylamino-6-methylchroman are obtained from 11.0 g (0.05 mol) of 4-amino-2,2-diethyl-6-methylchroman, 20.2 g (0.2 mol) of triethylamine and 7.7 g (0.06 mol) of ethanesulfonyl chloride in 140 ml THF analogously to Example 1c.

d) 2.0 g (6.4 mmol) of 2,2-diethyl-4-ethylsulfonylamino-6-methylchroman dissolved in 23 ml of DMF are added dropwise to a suspension of 0.22 g (7.4 mmol) of sodium hydride (80 percent dispersion) in 16 ml of DMF. After stirring at RT for 1 h, 1.0 g (6.6 mmol) of ethyl bromoacetate is added and the mixture is stirred overnight at RT. The DMF is then distilled off in vacuo, the residue is shaken with water and ethyl acetate and the organic phase is washed with dil. hydrochloric acid and sodium bicarbonate solution. After purification by chromatography using cyclohexane/EA 98:2, 1.35 g of methyl [(2,2-diethyl-6-methylchroman-4-yl) ethylsulfonylamino]-acetate are obtained.

e) By hydrolysis of 1.0 g (2.6 mmol) of methyl [(2,2-diethyl-6-methylchroman-4-yl)ethylsulfonylamino]acetate with 0.44 g (7.8 mmol) of KOH analogously to Example 2a, 0.89 g of [(2,2-diethyl-6-methylchroman-4-yl) ethylsulfonylamino]acetic acid is obtained.

f) A solution of 0.5 g (1.35 mmol) of [(2,2-diethyl-6-methylchroman-4-yl)ethylsulfonylamino]acetic acid, 0.2 g (1.5 mmol) of diethylene glycol monoethyl ether, 0.31 g (1.5 mmol) of DCC and 2 mg (0.01 mmol) of DMAP in 7 ml of methylene chloride is stirred overnight at RT. It is washed successively with 5% strength acetic acid, saturated sodium bicarbonate solution and water, dried over magnesium sulfate and concentrated in vacuo. After subsequent purification by chromatography using cyclohexane/EA 4:1, 0.29 g of 2-(2-ethoxyethoxy)ethyl [(2,2-diethyl-6-methylchroman-4-yl)ethylsulfonylamino]acetate is obtained as a viscous oil.

EXAMPLE 5
2-[Ethylsulfonyl-(6-fluoro-2,2-dimethylchroman-4-yl) amino]acetamide

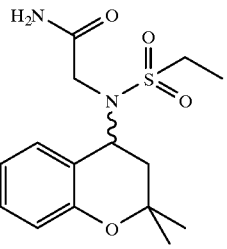

a) Analogously to the procedure indicated in Example 1a, 6-fluoro-2,2-dimethyl-4-chromanone is obtained from 5-fluoro-2-hydroxyacetophenone and acetone in the presence of pyrrolidine.

b) By heating 10 mmol of 6-fluoro-2,2-dimethyl-4-chromanone with 12 mmol of hydroxylamine hydrochloride in 5 ml of methanol and 5 ml of pyridine for 2 hours to 80° C., after distilling off the solvent and precipitating with water, 6-fluoro-2,2-dimethyl-4-chromanone oxime is obtained; m.p. 108–110° C.

c) By catalytic hydrogenation of 6-fluoro-2,2-dimethyl-4-chromanone oxime in methanol in an autoclave at 60° C. and 100 atm. hydrogen pressure in the presence of Raney nickel, 4-amino-6-fluoro-2,2-dimethyl-4-chroman is obtained (m.p. of the hydrochloride 226° C.).

d) 4-N-ethylsulfonylamino-6-fluoro-2,2-dimethylchroman is obtained as an amorphous product from 4-amino-6-fluoro-2,2-dimethyl-4-chroman analogously to procedure 1c.

e) 287 mg (1 mmol) of 4-N-ethylsulfonylamino-6-fluoro-2,2-dimethylchroman are dissolved in 5 ml of anhydrous DMA and treated with 45 mg (1.1 mmol) of NaH (60% strength). After stirring at RT for 30 min, 137 mg (1 mmol) of bromoacetamide are added and the mixture is stirred overnight at RT. After removing the DMA in vacuo, EA is added and the solvent is again removed in vacuo. The residue is dissolved in ethyl acetate and washed with sodium hydrogencarbonate solution and water. After drying and removing the solvent in vacuo, 340 mg (99%) of 2-[ethylsulfonyl-(6-fluoro-2,2-dimethylchroman-4-yl) amino]acetamide are obtained as a solid (m.p. 100–102° C.).

EXAMPLE 6
3-[Ethylsulfonyl-(6-fluoro-2,2-dimethylchroman-4-yl) amino]propionamide

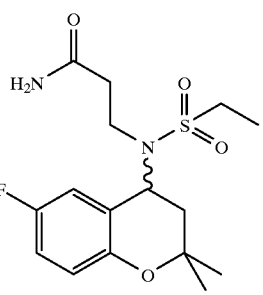

Analogously to Example 5, 180 mg (50%) of 3-[ethylsulfonyl-(6-fluoro-2,2-dimethylchroman-4-yl) amino]propionamide are obtained from 287 mg of 4-N-ethylsulfonylamino-6-fluoro-2,2-dimethylchroman and 151 mg of bromopropionamide as a solid (m.p. 134–136° C.).

EXAMPLE 7
2-[Ethylsulfonyl-(6-fluoro-2,2-dimethylchroman-4-yl) amino]-N-(3-imidazol-1-ylpropyl)acetamide

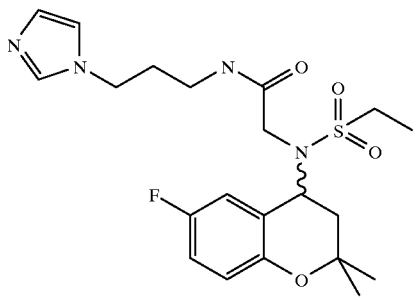

a) 5.74 g (20 mmol) of 4-N-ethylsulfonylamino-6-fluoro-2,2-dimethylchroman (Example 5d) are dissolved in 100 ml of anhydrous DMA and treated with 1 g (25 mmol) of NAH (60% strength). After stirring at RT for 40 min, 3 ml (27 mmol) of ethyl bromoacetate are added and the mixture is stirred overnight at RT. After removing the DMA in vacuo, EA is added and the solvent is again removed in vacuo. The residue is stirred with water and filtered off with suction. After reprecipitation from ethanol/water, 7.2 g (96%) of ethyl [ethylsulfonyl-(6-fluoro-2,2-dimethylchroman-4-yl) amino]acetate (m.p. 113–114° C.) are obtained.

b) 5.6 g (15 mmol) of ethyl [ethylsulfonyl-(6-fluoro-2,2-dimethylchroman-4-yl)amino]acetate are stirred overnight in a mixture of 200 ml of methanol and 75 ml of 2N NaOH. After distilling off the methanol in vacuo, the residue is washed with 100 ml of methylene chloride and acidified with conc. HCl. After extraction with methylene chloride and removal of the solvent in vacuo, 4.65 g (90%) of [ethylsulfonyl-(6-fluoro-2,2-dimethyl-chroman-4-yl)amino] acetic acid are obtained as a foam (m.p. 154–156° C.).

c) 210 mg (0.6 mmol) of [ethylsulfonyl-(6-fluoro-2,2-dimethylchroman-4-yl)-amino]acetic acid and 110 mg (0.68 mmol) of carbonylbisimidazole are stirred at RT for 2 hours in 6 ml of THF. 0.080 ml (0.67 mmol) of 3-aminopropylimidazole is then added and the mixture is stirred at RT overnight. It is then stirred with 60 ml of water and the THF is removed in vacuo. The residue is extracted twice with ethyl acetate, the organic phases are washed with 2N NaOH and water, and, after drying and removing the solvent, 210 mg (77%) of 2-[ethylsulfonyl-(6-fluoro-2,2-dimethylchroman-4-yl)amino]-N-(3-imidazol-1-yl-propyl) acetamide are obtained as an oil (m.p. of the hydrochloride: 188–190° C.).

EXAMPLE 8
2-[Ethylsulfonyl-(6-fluoro-2,2-dimethylchroman-4-yl)-amino]-N-(2-morpholin-4-ylethyl)acetamide

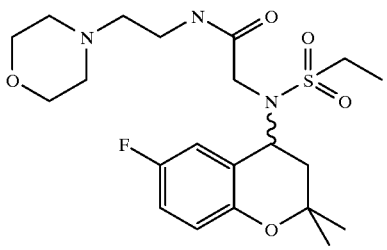

Analogously to Example 7, 325 mg (71%) of 2-[ethylsulfonyl-(6-fluoro-2,2-dimethylchroman-4-yl) amino]-N-(2-morpholin-4-ylethyl)acetamide are obtained from 345 mg (1 mmol) of [ethylsulfonyl-(6-fluoro-2,2-dimethylchroman-4-yl)amino]acetic acid and N-aminoethylmorpholine as an oil.

EXAMPLE 9
2-[Ethylsulfonyl-(6-fluoro-2,2-dimethylchroman-4-yl) amino]-N-(2-pyridin-2-ylethyl)acetamide

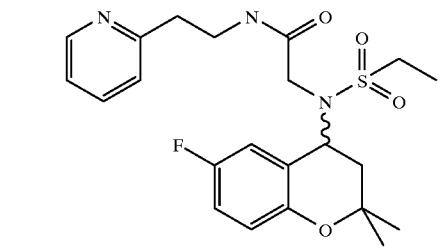

Analogously to Example 7, 250 mg (92%) of 2-[ethylsulfonyl-(6-fluoro-2,2-dimethylchroman-4-yl) amino]-N-(2-pyridin-2-yl-ethyl)acetamide are obtained from 210 mg (0.6 mmol) of [ethanesulfonyl-(6-fluoro-2,2-dimethylchroman-4-yl)amino]acetic acid and 80 μl of 2-aminoethylpyridine as an oil.

EXAMPLE 10
2-(Benzylmethylamino)ethyl 5-[methanesulfonyl-(2,2,6-trimethylchroman-4-yl)amino]pentanoate

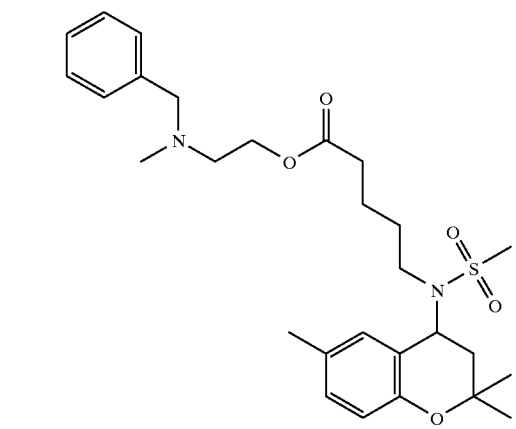

a) 40.2 g (0.40 mol) of triethylamine and 12.5 g (0.11 mol) of methanesulfonyl chloride are successively added dropwise to a solution of 19.0 g (0.099 mol) of 4-amino-2,2,6-trimethylchroman (Example 1b) in 300 ml of THF with cooling in an ice bath. After stirring overnight at RT, 300 ml of water are added, and the reaction mixture is concentrated to 200 ml and then diluted with a further 300 ml of water. The precipitate which is deposited is filtered off with suction and dried in vacuo, and 24.7 g of 4-methylsulfonylamino-2,2,6-trimethylchroman, m.p. 109–111° C., are obtained.

b) 26.6 g of methyl 5-[methylsulfonyl-(2,2,6-trimethylchroman-4-yl)amino]pentanoate are obtained from 19.5 g of 4-methylsulfonylamino-2,2,6-trimethylchroman analogously to Example 1d.

c) By hydrolysis of 20 g of methyl 5-[methylsulfonyl-(2,2,6-trimethylchroman-4-yl)amino]pentanoate with KOH in methanol/water, 13.8 g of 5-[methylsulfonyl-(2,2,6-trimethylchroman-4-yl)amino]pentanoic acid are obtained, m.p. 105–107° C.

d) A solution of 0.5 g (1.35 mmol) of 5-[methylsulfonyl-(2,2,6-trimethylchroman-4-yl)amino]pentanoic acid, 0.25 g (1.5 mmol) of 2-(N-benzyl-N-methylamino)ethanol, 0.31 g (1.5 mmol) of DCC and a spatula tipful of DMAP in 10 ml of methylene chloride is stirred overnight at RT. After filtering off the precipitate, the solution is concentrated and the crude product is purified by chromatography on silica gel using methylene chloride/methanol 97:3, and 0.45 g of 2-(benzylmethylamino)ethyl 5-[methanesulfonyl-(2,2,6-trimethylchroman-4-yl)amino]pentanoate is obtained.

EXAMPLE 11

5-[Methylsulfonyl-(2,2,6-trimethylchroman-4-yl)amino]pentanoic acid (2-(2-pyridyl)ethyl)amide

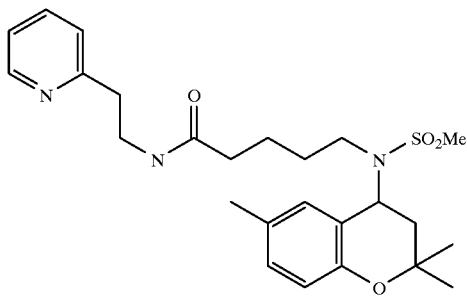

A mixture of 0.5 g (1.4 mmol) of 5-[methylsulfonyl-(2,2,6-trimethylchroman-4-yl)amino]pentanoic acid (Example 10c) and 0.26 g (1.6 mmol) of CDI in 20 ml of THF is stirred at RT for 3 h. 0.2 g (1.6 mmol) of 2-(2-aminoethyl)-pyridine is then added and the mixture is stirred further overnight at RT. After concentrating the reaction mixture, the residue is taken up in EA and water, and the organic phase is washed 3 times with 2M sodium hydroxide solution. After drying over magnesium sulfate, concentration and purification by chromatography on silica gel using methylene chloride/methanol 9:1, 0. 0.33 g of 5-[methylsulfonyl-(2,2,6-trimethylchroman-4-yl)amino]-pentanoic acid (2-(2-pyridyl)ethyl)amide is obtained.

EXAMPLE 12

5-[Methylsulfonyl-(2,2,6-trimethylchroman-4-yl)amino]-pentanoic acid (2-pyridylmethyl)amide

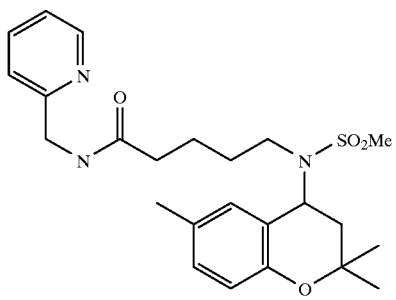

0.3 g of 5-[methylsulfonyl-(2,2,6-trimethylchroman-4-yl)amino]pentanoic acid (2-pyridylmethyl)amide is obtained from 0.5 g (1.4 mmol) of 5-[methylsulfonyl-(2,2,6-trimethylchroman-4-yl)amino]pentanoic acid (Example 10c) and 0.18 g (1.6 mmol) of 2-picolylamine analogously to Example 11.

EXAMPLE 13

2-[(6-Fluoro-2,2-dimethylchroman-4-yl)ethanesulfonylamino]-N-(1H-pyrazol-3-yl)acetamide

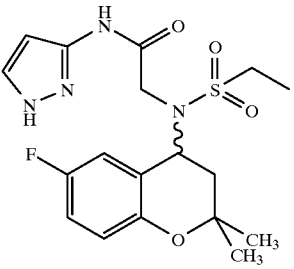

Analogously to Example 7, 260 mg of the substance having a melting point of 191° C. are obtained.

EXAMPLE 14

2-[(6-Fluoro-2,2-dimethylchroman-4-yl)ethanesulfonylamino]-N-pyridin-2-ylacetamide

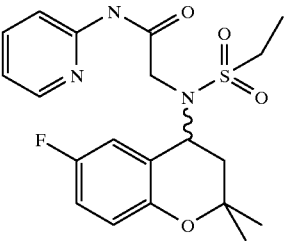

Analogously to Example 7, 280 mg of the substance having a melting point of 68° C. are obtained.

EXAMPLE 15

2-[(6-Fluoro-2,2-dimethylchroman-4-yl)ethanesulfonylamino]-N-[2-(5-nitropyridin-2-yl)ethyl]acetamide

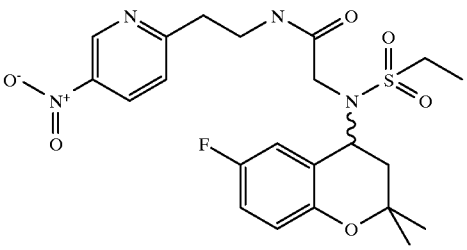

Analogously to Example 7, 180 mg of the substance having a melting point of 155° C. are obtained.

EXAMPLE 16

N-[2-(5-Aminopyridin-2-yl)ethyl]-2-[(6-fluoro-2,2-dimethylchroman-4-yl)ethanesulfonylamino]acetamide

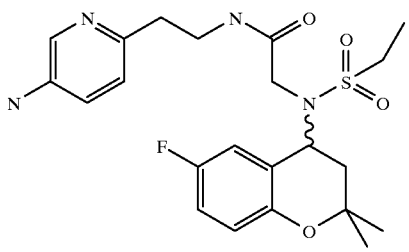

230 mg of 2-[(6-fluoro-2,2-dimethylchroman-4-yl)ethanesulfonylamino]-N-[2-(5-nitropyridin-2-yl)ethyl]acetamide (Example 15) are dissolved in 10 ml of EA and treated with 1.1 g of tin chloride hydrate and refluxed for 2 h. The mixture is treated with NaHCO₃ solution until it has an alkaline reaction. The inorganic salts are filtered off with suction and the EA phase is dried and the solvent is removed in vacuo. The crude product is treated with ethanolic HCl and concentrated. After treating with water, the residue is washed with EA. The water phase is rendered alkaline with sodium carbonate and extracted with EA. After removing the solvent, 75 mg of the product are obtained as an oil.

EXAMPLE 17
2-[(6-Benzyloxy-2,2-dimethylchroman-4-yl)methanesulfonylamino]-N-(2-pyridin-2-yl-ethyl)acetamide

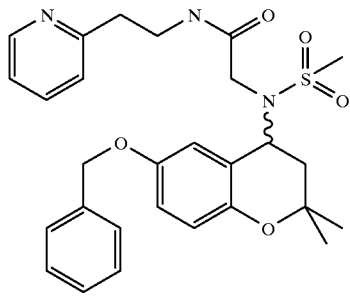

a) Methyl [(6-benzyloxy-2,2-dimethylchroman-4-yl)methanesulfonylamino]-acetate 1.08 g of 6-benzyloxy-4-(methylsulfonyl)amino-2,2-dimethylchroman (Example 28e) are dissolved in 15 ml of anhydrous DMA and stirred at RT for 45 min with 160 mg of NaH (60% strength). 0.5 ml of methyl bromoacetate is added and the mixture is stirred at RT for 14 h. After removing the solvent in vacuo, the residue is taken up in EA and washed with water. After drying and removing the solvent in vacuo, 1.4 g of methyl [(6-benzyloxy-2,2-dimethylchroman-4-yl)methanesulfonylamino]acetate are obtained as an oil.

b) [(6-Benzyloxy-2,2-dimethylchroman-4-yl)methanesulfonylamino]acetic acid 1.4 g of methyl [(6-benzyloxy-2,2-dimethylchroman-4-yl)methanesulfonylamino]acetate are stirred at RT for 4 h in 50 ml of methanol and 15 ml of 2N NaOH. After removing the methanol, the residue is washed with EA and acidified with HCl. It is extracted with EA and the solvent is removed in vacuo after drying. 500 mg of the acid having a melting point of 167–169° C. are obtained.

c) 2-[(6-Benzyloxy-2,2-dimethylchroman-4-yl)methanesulfonylamino]-N-(2-pyridin-2-yl-ethyl)acetamide The product is obtained analogously to the procedure in Example 7 from [(6-benzyloxy-2,2-dimethylchroman-4-yl)methanesulfonylamino]acetic acid, and the corresponding amine using carbonylbisimidazole. M.p. 131° C.

EXAMPLE 18
4-[Ethanesulfonyl-(6-fluoro-2,2-dimethylchroman-4-yl)amino]-N-(2-pyridin-2-yl-ethyl)butyramide

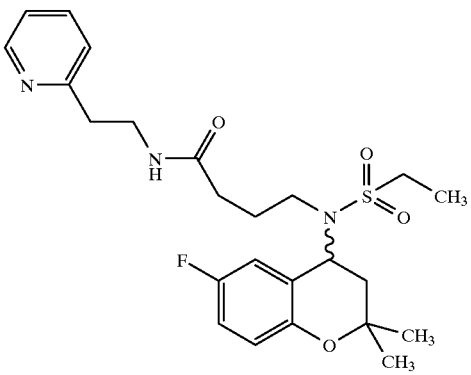

a) Ethyl 4-[ethanesulfonyl-(6-fluoro-2,2-dimethylchroman-4-yl)amino]-butanoate is obtained from ethylsulfonylamino-6-fluoro-2,2-dimethyl-4-chroman (Example 5d) in an analogous reaction to Example 7a using ethyl 4-bromobutyrate instead of ethyl bromoacetate.

b) 4-[Ethanesulfonyl-(6-fluoro-2,2-dimethylchroman-4-yl)amino]butanoic acid is obtained analogously to Example 7b.

c) 4-[Ethanesulfonyl-(6-fluoro-2,2-dimethylchroman-4-yl)amino]-N-(2-pyridin-2-yl-ethyl)butyramide is obtained analogously to reaction 7c as an oil.

EXAMPLE 19
2-[Ethanesulfonyl-(6-fluoro-2,2-dimethylchroman-4-yl)amino]-N-(2-piperidin-1-yl-ethyl)acetamide

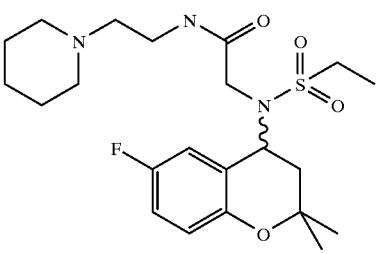

Analogously to Example 7, 180 mg of the substance are obtained as an oil.

EXAMPLE 20
2-[Ethanesulfonyl-(6-fluoro-2,2-dimethylchroman-4-yl)amino]-N-(2-piperazin-1-yl-ethyl)acetamide dihydrochloride

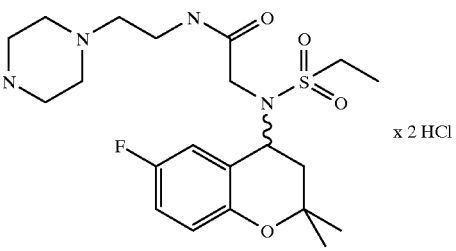

Analogously Example 7, 260 mg of the substance are obtained as an oil.

EXAMPLE 21

2-[Ethanesulfonyl-(6-fluoro-2,2-dimethylchroman-4-yl)amino]-N-phenethylacetamide

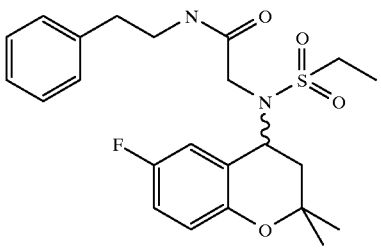

Analogously to Example 7, 270 mg of the substance having a melting point of 130° C. are obtained.

EXAMPLE 22

2-[Ethanesulfonyl-(6-fluoro-2,2-dimethylchroman-4-yl)amino]-N-pyridin-4-ylacetamide

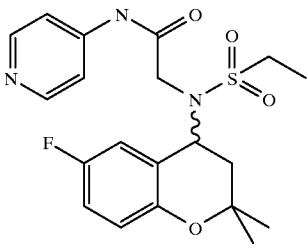

a) [Ethanesulfonyl-(6-fluoro-2,2-dimethylchroman-4-yl)amino]acetyl chloride 3.45 g of [ethanesulfonyl-(6-fluoro-2,2-dimethylchroman-4-yl)amino]acetic acid (Example 7b) are dissolved in 20 ml thionyl chloride and heated to reflux for 2 h. After removing the thionyl chloride in vacuo, the residue is diluted once each with toluene and methylene chloride and these solvents are removed in vacuo. 3.7 g of the acid chloride are obtained as an oil.

b) 2-[Ethanesulfonyl-(6-fluoro-2,2-dimethylchroman-4-yl)amino]-N-pyridin-4-ylacetamide 141 mg of p-aminopyridine and a spatula tipful of DMAP dissolved in 6 ml of pyridine are treated with a solution of 655 mg of [ethanesulfonyl-(6-fluoro-2,2-dimethylchroman-4-yl)amino]acetyl chloride in 6 ml of methylene chloride. The mixture is stirred at RT for 4 h and then concentrated in vacuo. The product is partitioned between EA and water and the organic phase is washed with water. After removing the solvent in vacuo, 600 mg of the product are obtained as a colorless foam (m.p. 195° C.).

EXAMPLE 23

2-[Ethanesulfonyl-(6-fluoro-2,2-dimethylchroman-4-yl)-amino]N-pyridin-3-ylacetamide

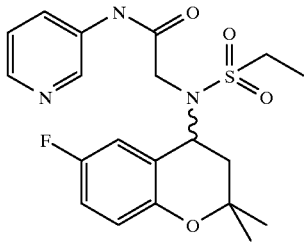

Analogously to Example 22, 390 mg of the substance are obtained as an oil.

EXAMPLE 24

2-[Ethanesulfonyl-(6-fluoro-2,2-dimethylchroman-4-yl)amino]-N-pyrimidin-2-ylacetamide

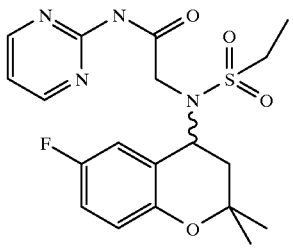

Analogously to Example 22, 370 mg of the substance are obtained as an oil.

EXAMPLE 25

2-[Ethanesulfonyl-(6-fluoro-2,2-dimethylchroman-4-yl)amino]-N-pyrazin-2-ylacetamide

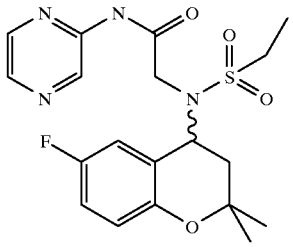

Analogously to Example 22, 220 mg of the substance are obtained as a solid (m.p. 189° C.).

EXAMPLE 26

N-Benzothiazol-2-yl-2-[ethanesulfonyl-(6-fluoro-2,2-dimethylchroman-4-yl)amino]acetamide

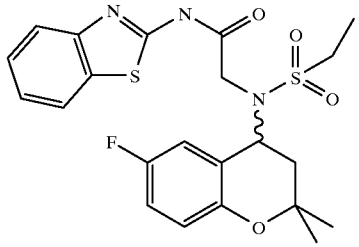

Analogously to Example 22, 370 mg of the substance are obtained as a solid (m.p. 114° C.).

EXAMPLE 27
2-[Ethanesulfonyl-(6-fluoro-2,2-dimethylchroman-4-yl)amino]-N-(1-methyl-1H-benzoimidazol-2-yl)acetamide

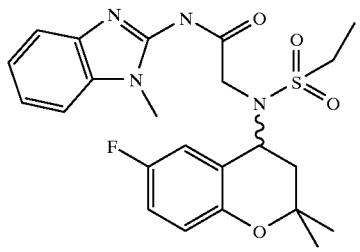

Analogously to Example 22, 470 mg of the substance are obtained as an oil.

EXAMPLE 28
4-[(6-Benzyloxy-2,2-dimethylchroman-4-yl)methanesulfonylamino]-N-butylbutyramide

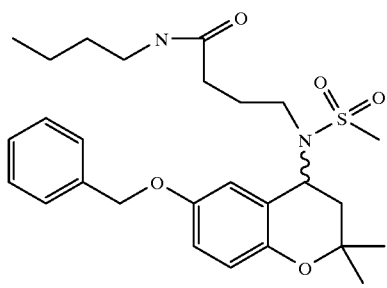

a) 2,2-Dimethyl-6-hydroxychroman-4-one

A reaction mixture of 100 g (0.65 mol) of 2,5-dihydroxycetophenone in 1 l of acetonitrile, 130 ml (1.55 mol) of pyrrolidine and 290 ml (3.95 mol) of acetone was heated to 45° C. for 8 h. The solvents were then stripped off in vacuo and the residue was dissolved in 1 l of EA. The organic phase was washed twice with dilute hydrochloric acid, stirred with activated carbon and dried over magnesium sulfate and largely concentrated. After stirring the residue with petroleum ether and filtering off the precipitate with suction, 102 g of 2,2-dimethyl-6-hydroxychroman-4-one, m.p. 158° C., were obtained.

b) 6-Benzyloxy-2,2-dimethylchroman-4-one 25.2 g (131.2 mmol) of 6-hydroxy-2,2-dimethylchroman-4-one were introduced into 350 ml of diethyl ketone with stirring at RT and, after addition of 18.0 g (131 mmol) of powdered potassium carbonate, the mixture was stirred at 75° C. for 30 min. After cooling to 60° C., 15.7 ml (131 mmol) of benzyl bromide were added dropwise, and after 2 h the mixture was concentrated in vacuo, the residue was treated with water and the solid was filtered off with suction, 37 g, m.p. 105–107° C.

c) 6-Benzyloxy-2,2-dimethylchroman-4-one oxime

By heating 11.3 g (40 mmol) of 6-benzyloxy-2,2-dimethylchroman-4-one with 3.1 g (44 mmol) of hydroxylamine hydrochloride in 27 ml of ethanol and 27 ml of pyridine for 3 h at 70° C., after distilling off the solvent in vacuo and precipitating with water, 12.5 g of product, m.p. 105–108° C., were obtained. The product was dissolved in EA, the solution was dried and concentrated, and the residue was crystallized using petroleum ether; m.p. 118–120° C.

d) 4-Amino-6-benzyloxy-2,2-dimethylchroman 30 g of 6-benzyloxy-2,2-dimethylchroman-4-one oxime were dissolved in 900 ml of THF/methanol (1:1), treated with 25 ml of aqueous ammonia and hydrogenated in a shaking duck using Raney Ni. The catalyst was then filtered off with suction, the filtrate was concentrated in vacuo, the residue was dissolved in EA, dried and concentrated, and the residue was crystallized using petroleum ether, 22.9 g, m.p. 86–88° C.

e) 6-Benzyloxy-4-(methylsulfonyl)amino-2,2-dimethylchroman 4.0 g (14 mmol) of 4-amino-6-benzyloxy-2,2-dimethylchroman were treated with 4.2 ml (30 mmol) of triethylamine in 80 ml of THF at RT and the mixture was stirred for 30 min, then treated with 1.95 g (1.3 ml, 17 mmol) of methanesulfonyl chloride, the temperature rising to 40° C. It was then heated to reflux for 2 h, allowed to stand overnight at RT and concentrated in vacuo, and the residue was treated with water; 4.9 g of product, m.p.162–165° C.

f) Ethyl 4-[(6-benzyloxy-2,2-dimethylchroman-4-yl)methanesulfonylamino]-N-butyrate 9.0 g (25 mmol) of 6-benzyloxy-4-(methylsulfonyl)amino-2,2-dimethylchroman were added in portions with stirring under a nitrogen atmosphere to a solution of 1.8 g (45 mmol) of NaH (about 60% strength dispersion in mineral oil) in 100 ml of DMA and the mixture was stirred at 45° C. for 30 min. 5.3 ml (30 mmol) of ethyl 4-bromobutryate were then added dropwise and the mixture was heated at 110° C. for 90 min. After cooling, it was concentrated in vacuo, the residue was treated with 1 N aqueous hydrochloric acid, taken in EA, dried and concentrated, and the residue was chromatographed on silica gel using heptane/EA 2:1. Appropriate fractions were crystallized using PE/DIPE; 10.1 g, m.p. 78–80° C.

g) 4-[(6-Benzyloxy-2,2-dimethylchroman-4-yl)methanesulfonylamino]-N-butyric acid 7.0 g of the above ethyl ester were introduced into 200 ml of 1.5 N methanol NaOH and the mixture was stirred at 45° C. for 1 h. It was then concentrated, the residue was dissolved in 150 ml of water, the solution was brought to pH 1 with cooling using conc. hydrochloric acid, the resinous residue was taken up in EA, the solution was dried and concentrated, and the residue was crystallized using PE; 6.4 g of product, m.p. 138–140° C.

h) 3.1 g of the above carboxylic acid were reacted with 3 drops of N,N-dimethylacetamide and 1.2 ml (14 mmol) of oxalyl chloride in 80 ml of THF and 1.4 ml (14 mmol) of butylamine in a little THF were added dropwise to this solution at 5° C. After 30 min, it was concentrated, treated with 1N aqueous hydrochloric acid, the residue was taken up in EA and dried, the solution was concentrated and the residue was chromatographed on silica gel using EA. 1.6 g of 4-[(6-benzyloxy-2,2-dimethylchroman-4-yl)methanesulfonylamino]-N-butylbutyramide were obtained as an oily product.

EXAMPLE 29
N-(6-Benzyloxy-2,2-dimethylchroman-4-yl)-N-[4-(2-methoxyethoxy)butyl]methanesulfonamide

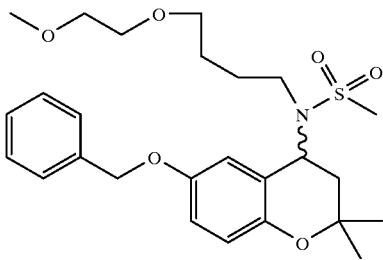

a) N-(6-Benzyloxy-2,2-dimethylchroman-4-yl)-N-[4-hydroxybutyl]methanesulfonamide 5.7 g (12 mmol) of ethyl 4-[(6-benzyloxy-2,2-dimethylchroman-4-yl)-methanesulfonylamino]-N-butyrate (Ex. 28f) were treated with 10 ml of 1 M lithium aluminum hydride solution in THF in 100 ml of THF at 0° C. The mixture was treated at RT with a little water, then with 1N hydrochloric acid, and concentrated, and the residue was extracted three times using EA. After drying and concentrating, the product crystallized overnight. 4.9 g were obtained, m.p. 113–115° C. (from PE/DIPE)

b) 0.52 g (1.2 mmol) of the above compound was stirred at 50° C. for 30 min in 20 ml of DMA with 0.12 g (3 mmol) of NaH. After addition of 0.5 ml (5 mmol) of 2-methoxyethyl bromide, the mixture was heated at 120° C. for 90 min. After addition of a further 0.36 g of NaH and 0.5 ml of bromide, the conversion was complete after 1 h at 120° C. After working up, the residue was chromatographed on silica gel using heptane/EA 1:1. 0.26 g of the oily title compound was obtained.

EXAMPLE 30

Ethyl {4-[(6-benzyloxy-2,2-dimethylchroman-4-yl)methanesulfonylamino]butoxy}acetate

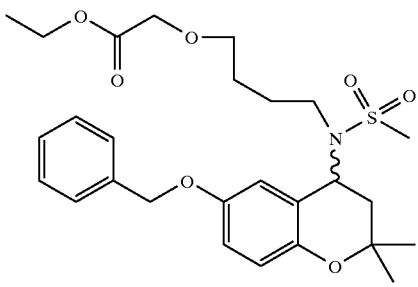

1.5 g (3.5 mmol) of N-(6-benzyloxy-2,2-dimethylchroman-4-yl)-N-4-hydroxybutyl]methanesulfonamide (Example 29a) were treated with 0.24 g (6 mmol) of NaH in 50 ml of DMA at RT under argon and the mixture was stirred at 50° C. for 30 min. 0.5 ml (4.5 mmol) of ethyl bromoacetate was then added dropwise and the mixture was heated at 80° C. for 1 h. Both reagents were added a further 2× in equal amounts and the mixture was then heated again in each case. After working up and column chromatography using heptane/EA 1:1 on silica gel, 0.7 g of the oily title compound was obtained from appropriate fractions.

EXAMPLE 31

Ethyl ({4-[(6-benzyloxy-2,2-dimethylchroman-4-yl)methanesulfonylamino]butyryl}methylamino)acetate

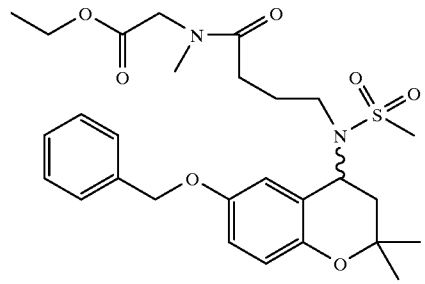

0.9 g (2 mmol) of 4-[(6-benzyloxy-2,2-dimethylchroman-4-yl)methanesulfonylamino]-N-butyric acid (Example 28g) was treated with 0.42 g (2.5 mmol) of N,N-carbonyldiimidazole in 50 ml of THF at RT with stirring and the mixture was stirred at 60° C. for 1 h. A suspension of sarcosine ethyl ester hydrochloride and triethylamine in THF was then added and the mixture was heated at 60° C. for 2 h. After working up, 0.75 g of resinous product was obtained from EA.

EXAMPLE 32

Ethyl ({2-[(6-benzyloxy-2,2-dimethylchroman-4-yl)methanesulfonylamino]acetyl}methylamino)acetate

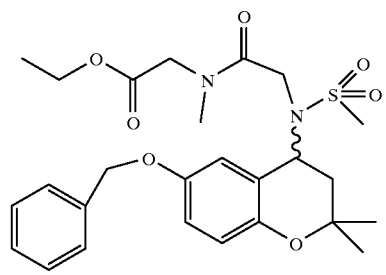

a) Ethyl 4-[(6-benzyloxy-2,2-dimethylchroman-4-yl)methanesulfonylamino]-N-acetate 3.6 g (10 mmol) of 6-benzyloxy-4-(methylsulfonyl)amino-2,2-dimethylchroman (Example 28 e) were added in portions with stirring under a nitrogen atmosphere to a solution of 0.72 g (18 mmol) of NaH in 50 ml of DMA and the mixture was stirred at 50° C. for 30 min. 1.5 ml (13.5 mmol) of ethyl bromoacetate were then added dropwise and the mixture was heated at 110° C. for 120 min. After cooling, it was concentrated in vacuo, the residue was treated with 1 N aqueous hydrochloric acid, taken up in EA, the solution was dried and concentrated, and the residue was chromatographed on silica gel using heptane/EA 3:1. Appropriate fractions were crystallized using PE; 3.6 g, m.p. 119–121° C.

b) 4-[(6-Benzyloxy-2,2-dimethylchroman-4-yl)methanesulfonylamino]-N-acetic acid 7.0 g of the above ethyl ester were introduced into 250 ml of 1.5 N methanolic NaOH and the mixture was stirred at 50° C. for 1 h. It was then concentrated, the residue was dissolved in 150 ml of water and brought to pH 1 with cooling using conc. hydrochloric acid, the resinous residue was taken up in EA, the solution was dried and concentrated, and the residue was crystallized using PE; 6.2 g of product, m.p. 177–179° C.

c) 0.525 g (1.25 mmol) 4-[(6-benzyloxy-2,2-dimethylchroman-4-yl)methanesulfonylamino]-N-acetic acid was treated with 0.248 g (1.5 mmol) of N,N'- carbonyldiimidazole in 50 ml of THF at RT with stirring and the mixture was stirred at 60° C. for 1 h. A suspension of 0.184 g (1.2 mmol) of sarcosine ethyl ester hydrochloride and 0.18 ml (1.3 mmol) of triethylamine in THF was then added and the mixture was heated to 60–70° C. for 2 h. After working up, 0.55 g of oily product were obtained from EA.

EXAMPLE 33
4-[(6-Benzyloxy-2,2-dimethylchroman-4-yl)methanesulfonylamino]-N-(2-piperidin-1-yl-ethyl)butyramide hydrochloride

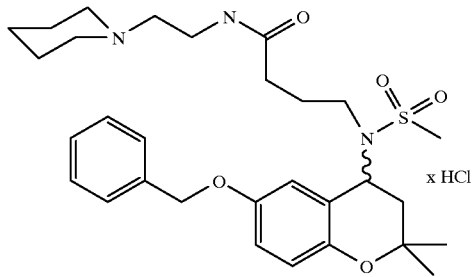

0.7 g (1.5 mmol) of 4-[(6-benzyloxy-2,2-dimethylchroman-4-yl)methanesulfonylamino]-N-butyric acid (Example 28g) was stirred at 60° C. for 1 h in 40 ml of THF with 0.35 g (2 mmol) of N,N'-carbonyldiimidazole. 1 ml (about 6 mmol) of 2-aminoethylpiperidine was then added, the mixture was stirred at 60° C. for 3 h and concentrated, the residue was treated with water, the mixture was extracted with EA, the organic phase was dried and concentrated and the residue was purified on silica gel using EA/methanol 2:1. 0.65 g of the oil obtained was treated with ethereal hydrochloric acid in THF, concentrated and crystallized using PE; 0.56 g, m.p.178–180° C.

EXAMPLE 34
{4-[(6-Benzyloxy-2,2-dimethylchroman-4-yl)methanesulfonylamino]butoxy}acetic acid

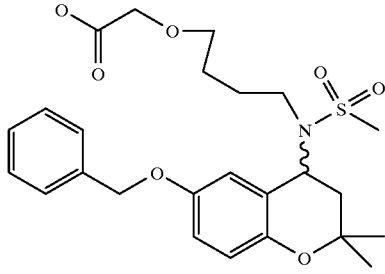

0.3 g of ethyl {4-[(6-benzyloxy-2,2-dimethylchroman-4-yl)-methanesulfonylamino]butoxy}acetate (Example 30) was hydrolyzed at 40° C. for 30 min in 25 ml of 1.5 N methanolic NaOH. The mixture was then concentrated, brought to pH 1 using hydrochloric acid, precipitated resin was taken up in EA, the solution was dried and concentrated and the residue was crystallized using DIPE; 90 mg of product, m.p. 110–113° C.

EXAMPLE 35
({4-[(6-Benzyloxy-2,2-dimethylchroman-4-yl)methanesulfonylamino]butyryl}methylamino)acetic acid

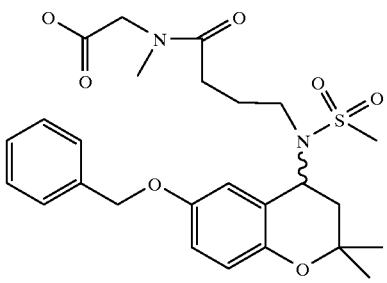

0.4 g (0.75 mmol) of ethyl ({4-[(6-benzyloxy-2,2-dimethylchroman-4-yl)-methanesulfonylamino]butyryl}methylamino)acetic acid (Example 31) was hydrolyzed at RT for 2 h in 50 ml of 1 N methanolic NaOH. After working up (THF, aqueous hydrochloric acid, EA), 0.34 g of the title compound was crystallized using DIPE, m.p. about 50° C.

EXAMPLE 36
4-({4-[(6-Benzyloxy-2,2-dimethylchroman-4-yl)methanesulfonylamino]butyryl}methylamino)butyric acid

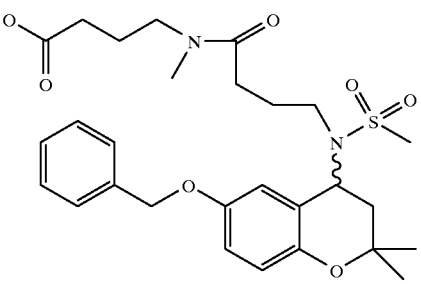

0.7 g (1.5 mmol) of 4-[(6-benzyloxy-2,2-dimethylchroman-4-yl)methanesulfonylamino]-N-butyric acid (Example 28 g) was stirred at 60° C. for 1 h in 40 ml of THF with 0.35 g (2 mmol) of N,N'-carbonyldiimidazole. 0.62 g (4 mmol) of 4-methylaminobutyric acid hydrochloride in 25 ml of THF and 1.3 ml of triethylamine were then added and the mixture was heated to reflux for 3 h. After working up, 0.11 g of the title compound was isolated as a resin.

EXAMPLE 37
4-({2-[(6-Benzyloxy-2,2-dimethylchroman-4-yl)methanesulfonylamino]acetyl}methylamino)butyric acid

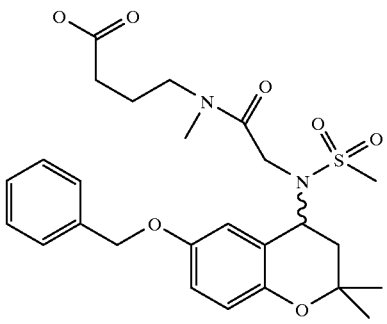

0.525 g (1.25 mmol) of 4-[(6-benzyloxy-2,2-dimethylchroman-4-yl)-methanesulfonylamino]-N-acetic acid was treated with 0.248 g (1.5 mmol) of N,N'- carbonyldiimidazole in 50 ml of THF at RT with stirring and the mixture was stirred at 60° C. for 1 h. A suspension of 0.184 g (1.2 mmol) of 4-(N-methylamino)butyric acid hydrochloride and 0.45 ml (3.25 mmol) of triethylamine in THF was then added at RT and the mixture was heated to 60–70° C. for 2 h. After working up, 0.406 g of amorphous product were obtained from EA.

EXAMPLE 38
N-(6-Benzyloxy-2,2-dimethylchroman-4-yl)-N-[2-(2-methoxyethoxy)ethyl]methanesulfonamide

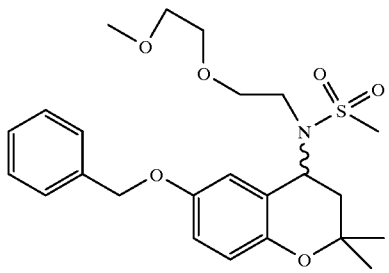

a) N-(6-Benzyloxy-2,2-dimethylchroman-4-yl)-N-[2-hydroxyethyl]methanesulfonamide 3.8 g (8.5 mmol) of ethyl 4-[(6-benzyloxy-2,2-dimethylchroman-4-yl)-methanesulfonylamino]-N-acetate (Example 32a) were treated with 8 ml of 1 M lithium aluminum hydride solution in THF in 80 ml of THF at 0° C. The mixture was treated at RT with a little water, then with 1 N hydrochloric acid, and concentrated and the residue was extracted 3 times with EA. After drying and concentrating, the crude product was chromatographed on silica gel using EA. 3.0 g of product were crystallized from appropriate fractions using DIPE, m.p. 78–80° C.

b) 0.49 g (1.2 mmol) of the above alcohol was treated with 216 mg (5.4 mmol) of NaH in 20 ml of DMA and the mixture was kept at 80–90° C. for 30 min. 0.4 ml (4 mmol) of 2-methoxyethyl bromide was then added at 60° C. and the mixture was stirred at 110° C. for 2 h. After working up and purification of the crude product using heptane/EA 1:1 on silica gel, 70 mg of the oily title compound were obtained.

EXAMPLE 39
2-[(6-Benzyloxy-2,2-dimethylchroman-4-yl) methanesulfonylamino]-N-methyl-N-phenethylacetamide

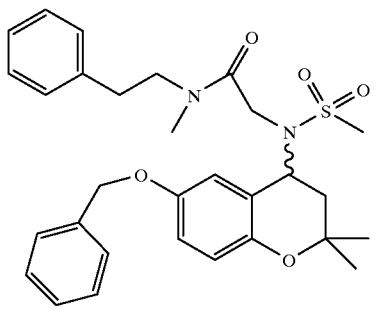

1.58 g (3.25 mmol) of 4-[(6-benzyloxy-2,2-dimethylchroman-4-yl)methanesulfonylamino]-N-acetic acid (Example 32b) were treated with 0.975 g (6 mmol) of N,N'-carbonyldiimidazole in 100 ml of THF at RT with stirring and the mixture was stirred at 60–70° C. for 1 h. A solution of 0.26 ml (1.8 mmol) of N-methyl-2-phenylethylamine and 0.25 ml (1.8 mmol) of triethylamine in THF was then added to half of this solution and it was heated to 60–70° C. for 2 h. After working up, the crude product was chromatographed on silica gel using heptane/EA 1:1. 0.7 g of the title compound was crystallized from appropriate fractions using DIPE, m.p. 106–107° C.

EXAMPLE 40
2-[(6-Benzyloxy-2,2-dimethylchroman-4-yl) methanesulfonylamino]-N-methyl-N-(2-pyridin-2-yl-ethyl) acetamide hydrochloride

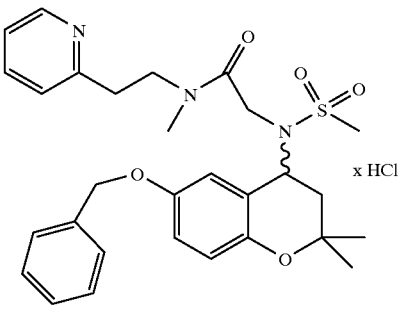

0.25 ml (1.8 mmol) of N-methyl-2-(2-pyridyl)ethylamine and 0.25 ml (1.8 mmol) of triethylamine in 30 ml of THF were added to the 2nd half of the activated carboxylic acid solution from Example 39 and it was heated under reflux for 2 h. 0.65 g of product crystallizes on cooling after working up from aqueous hydrochloric acid, m.p. 140–143° C.

EXAMPLE 41
Ethyl {2-[(6-butoxy-2,2-dimethylchroman-4-yl) methanesulfonylamino]ethoxy}acetate

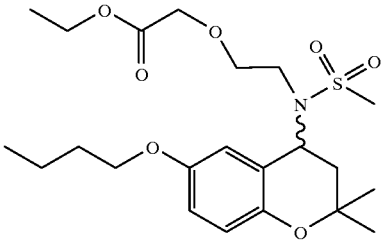

a) 6-Butoxy-2,2-dimethylchroman-4-one

A solution of 50 g (0.26 mol) of 2,2-dimethyl-6-hydroxychroman-4-one (Example 28a) in 500 ml of DMF was added dropwise to a suspension of 9.0 g (0.3 mol) of 80% sodium hydride in 500 ml of DMF. After stirring at RT for 90 min, 49 g (0.265 mol) of iodobutane were added and the mixture was stirred at RT for a further 90 min. The reaction mixture was then concentrated in vacuo, the residue was treated with water and the mixture was extracted several times with EA. The organic phases were washed with 5 M sodium hydroxide solution, stirred with activated carbon and magnesium sulfate, filtered and concentrated. 57.6 g of 6-butoxy-2,2-dimethylchroman-4-one were obtained.

b) 6-Butoxy-2,2-dimethylchroman-4-one oxime

A solution of 52.0 g (0.21 mol) of 6-butoxy-2,2-dimethylchroman-4-one in 420 ml of ethanol were added dropwise in 30 min to a solution of 43.7 g (0.628 mol) of hydroxylammonium chloride and 51.5 g (0.628 mol) of sodium acetate in 420 ml of water and the mixture was kept at 60° C. for 3 h. The oily product phase was separated off and the aqueous phase was extracted with methylene chloride. After drying the organic phases over magnesium sulfate and concentrating in vacuo, 55.5 g of 6-butoxy-2,2-dimethylchroman-4-one oxime were obtained, which it was possible to crystallize by stirring with PE.

c) 4-Amino-6-butoxy-2,2-dimethylchroman

A solution of 30 g of 6-butoxy-2,2-dimethylchroman-4-one oxime in 500 ml of methanol, 500 ml of THF and 30 ml of ammonia solution was hydrogenated in a shaking duck for 8 h in the presence of Raney nickel. After filtering off the catalyst and concentrating in vacuo, 20.5 g of 4-amino-6-butoxy-2,2-dimethylchroman were obtained.

d) 6-Butoxy-4-(methylsulfonyl)amino-2,2-dimethylchroman

A reaction mixture of 3.0 g (12 mmol) of 4-amino-6-butoxy-2,2-dimethylchroman, 4.9 g (48 mmol) of triethylamine and 1.65 g (14.4 mmol) of methanesulfonyl chloride in 25 ml of THF was stirred at RT for 3 h. After concentrating, the residue was taken up in water and extracted with EA. After drying and concentrating, the product was crystallized using PE and 2.25 g of 6-butoxy-4-(methylsulfonyl)amino-2,2-dimethylchroman were obtained; m.p. 123–127° C.

e) Ethyl 4-[(6-butoxy-2,2-dimethylchroman-4-yl)methanesulfonylamino]-N-acetate 5.9 g (18 mmol) of 6-butoxy-4-(methylsulfonyl)amino-2,2-dimethylchroman were added in portions with stirring under a nitrogen atmosphere to a solution of 1.16 g (29 mmol) of NaH in 80 ml of DMA and the mixture was stirred at 60–70° C. for 30 min. 2.53 ml (22 mmol) of ethyl bromoacetate were then added dropwise at 40° C. and the mixture was heated to 110° C. for 120 min. After cooling, it was concentrated in vacuo, the residue was treated with 1 N aqueous hydrochloric acid and taken up in EA, the solution was dried and concentrated, and the residue was chromatographed on silica gel using heptane/EA 3:1. Appropriate fractions were crystallized using DIPE; 5.2 g, m.p. 124–126° C.

f) 5.2 g (12.5 mmol) of ethyl 4-[(6-butoxy-2,2-dimethylchroman-4-yl)-methanesulfonylamino]-N-acetate were treated with 10 ml of 1 M lithium aluminum hydride solution in THF in 100 ml of THF at 0° C. The mixture was treated at RT with a little water, then with 1N hydrochloric acid, and concentrated, and the residue was extracted 3 times with EA. After drying and concentrating, 4.59 g of the corresponding alcohol were crystallized using DIPE; m.p.106–108° C.

g) 1.5 g (4 mmol) of the above alcohol were treated with 1.9 g (6 mmol) of phosphazene base P1 in 60 ml of anhydrous toluene and the mixture was heated to 80–90° C. for 30 min. 0.54 g (4.8 mmol) of ethyl bromoacetate was then added, the mixture was heated to reflux for 90 min, TLC checking, further addition of 1.9 ml of phosphazene base P1 and 1 ml of ethyl bromoacetate and heating to reflux for 2 h. After working up (concentration, aqueous hydrochloric acid, EA, drying), the residue was chromatographed on silica gel using toluene/EA 15:1 and 670 mg of oily product were obtained.

EXAMPLE 42

N-(6-Butoxy-2,2-dimethylchroman-4-yl)-N-[2-(2-methoxyethoxy)ethyl]methanesulfonamide

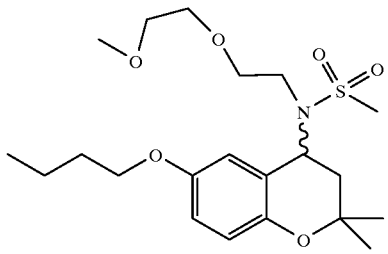

a) 1.37 g (3 mmol) of the ester from Example 41 g were treated with 3 ml of 1 M lithium aluminum hydride solution in THF in 50 ml of THF at 0° C. and the mixture was stirred at RT for 1 h. It was then treated with a little water, then with 1 N hydrochloric acid, and concentrated, and the residue was extracted 3 times with EA. After drying and concentrating, the crude product was chromatographed on silica gel using heptane/EA 1:1, 0.77 g of oily product which crystallized after 2 days at RT; m.p. 70–72° C.

b) The title compound was obtained by stirring 0.623 g (1.5 mmol) of the above alcohol in 20 ml of DMA at 80° C. for 20 min with 80 mg (2 mmol) of NaH, adding 0.6 ml (10.2 mmol) of methyl iodide at RT and then heating at 95–100° C. for 1 h. After TLC checking, further addition of 40 mg of NaH and 1 ml of methyl iodide and heating to 110–115° C. for a further 90 min took place. The crude product was purified on silica gel using heptane/EA and 85 mg of oily product were obtained.

EXAMPLE 43

{2-[(6-Butoxy-2,2-dimethylchroman-4-yl)methanesulfonylamino]ethoxy}acetic acid

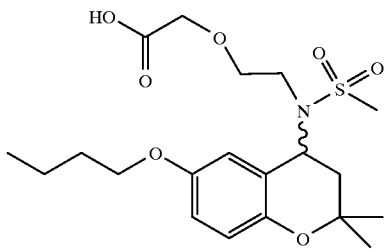

0.6 g of ethyl {2-[(6-butoxy-2,2-dimethylchroman-4-yl)methanesulfonylamino]ethoxy}acetate (Example 41g) was dissolved in a little methanol and stirred at RT for 60 min with a solution of 3.6 g of lithium hydroxide in 100 ml of methanol/water 3:1. After working up (aqueous hydrochloric acid, EA), 0.44 g of the resinous title compound was obtained, which crystallized after standing for several days; m.p. 82–84° C.

EXAMPLE 44

Ethyl {3-[(6-butoxy-2,2-dimethylchroman-4-yl)methanesulfonylamino]propoxy}acetate

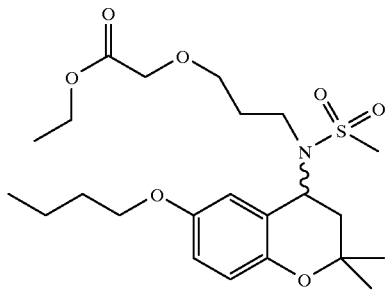

a) N-(6-Butoxy-2,2-dimethylchroman-4-yl)-N-[3-benzyloxypropyl]methanesulfonamide 320 mg (about 8 mmol) of NaH were added to 1.96 g (6 mmol) of 6-butoxy-4-(methylsulfonyl)amino-2,2-dimethylchroman (Example 41d) in 20 ml of DMA and the mixture was stirred at 70–80° C. for 30 min. 1.26 ml (about 7.5 mmol) of 3-benzyloxy-1-propyl bromide were then added at 50° C. and the mixture was stirred at 110° C. for 3.5 h. After working up (water, hydrochloric acid, EA), 2.7 g of oil were obtained from appropriate fractions after chromatography using toluene/EA 5:1 on silica gel.

b) N-(6-Butoxy-2,2-dimethylchroman-4-yl)-N-[3-hydroxypropyl]methanesulfonamide 2.5 g of the above benzyl compound were hydrogenated in the shaking duck in THF/methanol 1:1 using Pd/carbon (10%) (absorption about 170 ml of hydrogen). The catalyst was filtered off with suction, the solution was concentrated and the residue was crystsallized using DIPE/PE 1:2; 1.9 g, m.p. 69–71° C.

c) 1.6 g (4.15 mmol) of the above alcohol were heated with 1.4 g (4.5 mmol) of phosphazene base P1 in 50 ml of toluene and the mixture was heated to reflux for 2 h after addition of 0.54 ml (4.8 mmol) of ethyl bromoacetate. After working up, unreacted starting material was separated off by chromatography using toluene/ethyl acetate 15:1 on silica gel. 0.5 g of the above title compound was obtained, which became solid on standing at RT; m.p. 67–69° C.

EXAMPLE 45
N-(6-Butoxy-2,2-dimethylchroman-4-yl)-N-[3-(2-hydroxyethoxy)propyl]methanesulfonamide

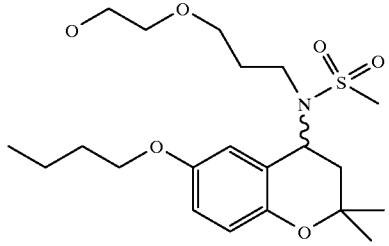

1.25 g (2.5 mmol) of the above ester (Example 44) were treated with 3.5 ml of 1 M lithium aluminum hydride solution in 40 ml of THF at 0° C. and the mixture was stirred at RT for 1 h. It was then treated with a little water, then with 1 N hydrochloric acid, and concentrated, and the residue was extracted twice with EA. After drying and concentrating, the crude product was chromatographed on silica gel using heptane/EA 1:2. 0.6 g of the oily title compound was obtained, which became waxy on standing at RT.

EXAMPLE 46
{3-[(6-Butoxy-2,2-dimethylchroman-4-yl) methanesulfonylamino]propoxy}acetic acid

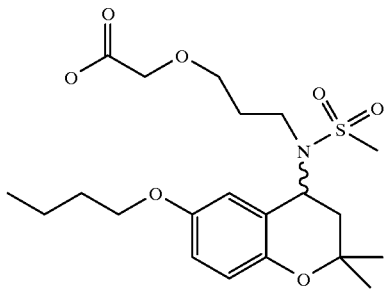

0.48 g of the ester from Example 45 was added to a clear solution of 2.4 g of lithium hydroxide in 100 ml of methanol/water 3:1. After 1 h at RT, the mixture was concentrated, the aqueous solution was extracted with diethyl ether and acidified with aqueous hydrochloric acid, and the crystalline precipitate was filtered off with suction, washed with water and dried. 0.36 g of the title compound was obtained; m.p. 79–81° C.

EXAMPLE 47

3-[(6-Butoxy-2,2-dimethylchroman-4-yl) methanesulfonylamino]propyl ($^2$-morpholin-4-yl-ethyl) carbamate

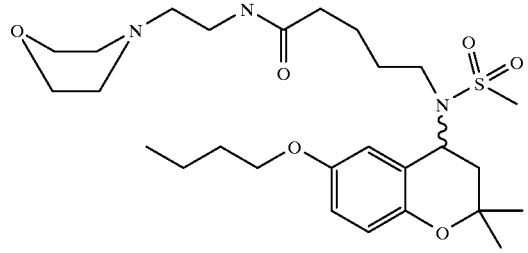

0.77 g (2 mmol) of N-(6-butoxy-2,2-dimethylchroman-4-yl)-N-[3-hydroxypropyl]methanesulfonamide (Example 44b) was treated with 96 mg (2.4 mmol) of NaH in 50 ml of THF with strring at RT and the mixture was heated to 50° C. for 5 min. This solution was added dropwise after cooling to a solution of 347 mg (2.1 mmol) of N,N'-carbonyidiimidazole in 40 ml of THF and the mixture was heated to reflux for 30 min. 780 mg (6 mmol) of 2-aminoethylmorpholine in 5 ml of THF were then added dropwise, the mixture was heated to reflux for 2 h and concentrated, the residue was treated with water, the mixture was extracted with diethyl ether, the ethereal phase was washed with aqueous hydrochloric acid, the acidic phase was brought to pH 8 and extracted with EA, and 0.7 g of resinous product was obtained.

EXAMPLE 48

5-[Methanesulfonyl-(2,2,6-trimethylchroman-4-yl)amino]-pentanoic acid guanidide hydrochloride

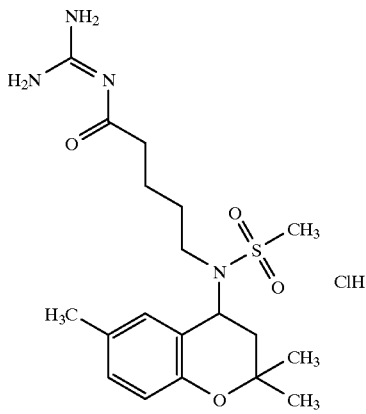

A mixture of 0.5 g (1.4 mmol) of 5-[methylsulfonyl-(2,2,6-trimethylchroman4-yl)amino]pentanoic acid (Example 10c) and 0.26 g (1.6 mmol) of CDI in 20 ml of THF was stirred at RT for 3 h. 0.45 g (8 mmol) of guanidine was then added and the mixture was stirred further overnight at RT. After concentrating the reaction mixture, the residue was treated with 50 ml of water, and stirred overnight at RT. The precipitated product was filtered off with suction and converted into the hydrochloride. 0.2 g of 5-[methanesulfonyl-(2,2,6-trimethylchroman-4-yl)amino]pentanoic acid guanidide hydrochloride was obtained; m.p. 190–195° C.

EXAMPLE 49

2-(Benzylmethylamino)ethyl [ethanesulfonyl-(6-fluoro-2,2-dimethylchroman-4-yl)amino]acetate

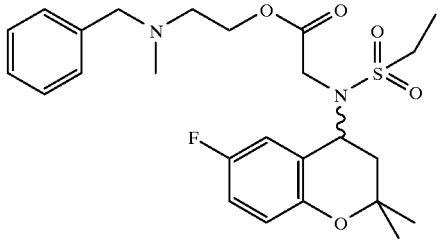

Analogously to Example 7, 270 mg (67%) of 2-(benzylmethylamino)ethyl [ethanesulfonyl-(6-fluoro-2,2-dimethylchroman-4-yl)amino]acetate are obtained from 310 mg (0.9 mmol) of [ethylsulfonyl-(6-fluoro-2,2-dimethylchroman-4-yl)amino]acetic acid and 165 mg (1.0 mmol) of 2-(benzylmethylamino)ethanol as a solid (m.p. 130° C.).

EXAMPLE 50

2-[Ethanesulfonyl-(6-fluoro-2,2-dimethylchroman-4-yl)amino]-N-(2-ethyl-2H-pyrazol-3-yl)acetamide

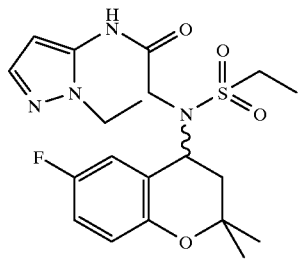

Analogously to Example 22, 440 mg (96%) of 2-[ethanesulfonyl-(6-fluoro-2,2-dimethylchroman-4-yl)amino]-N-(2-ethyl-2H-pyrazol-3-yl)acetamide are obtained from 380 mg (1,0 mmol) of [ethylsulfonyl-(6-fluoro-2,2-dimethylchroman-4-yl)amino]acetyl chloride and 111 mg (1 mmol) of 5-amino-1-ethylpyrazole as a solid (m.p. 69° C.).

EXAMPLE 51

N-(1H-benzimidazol-2-ylmethyl)-2-[ethanesulfonyl-(6-fluoro-2,2-dimethylchroman-4-yl)amino]acetamide

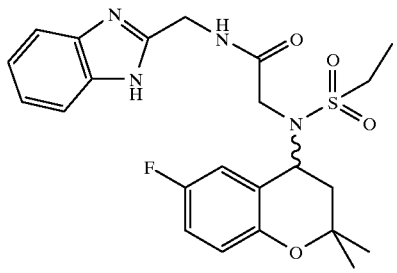

Analogously to Example 22, 470 mg (90%) of N-(1H-benzimidazol-2-ylmethyl)-2-[ethanesulfonyl-(6-fluoro-2,2-dimethylchroman-4-yl)amino]-acetamide are obtained from 420 mg (1.1 mmol) of [ethylsulfonyl-(6-fluoro-2,2-dimethylchroman-4-yl)amino]acetyl chloride and 220 mg (1 mmol) of 2-aminomethylbenzimidazole as an oil.

EXAMPLE 52

2-[Ethanesulfonyl-(6-fluoro-2,2-dimethylchroman-4-yl)amino]-N-isothiazol-5-ylacetamide

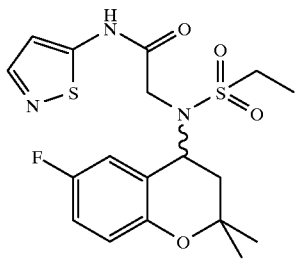

Analogously to Example 22, 430 mg (96%) of 2-[ethanesulfonyl-(6-fluoro-2,2-dimethylchroman-4-yl)amino]-N-isothiazol-5-ylacetamide are obtained from 380 mg (1.0 mmol) of [ethylsulfonyl-(6-fluoro-2,2-dimethylchroman-4-yl)amino]acetyl chloride and 100 mg (1 mmol) of 2-aminothiazole as a solid (m.p. 167° C.).

EXAMPLE 53

2-[Ethanesulfonyl-(6-fluoro-2,2-dimethylchroman-4-yl)amino]-N-(5-methylisoxazol-3-yl)acetamide

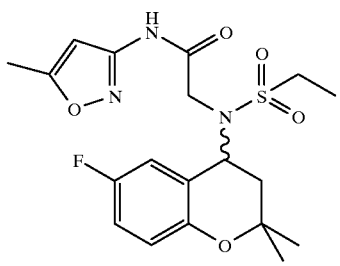

Analogously to Example 22, 425mg (95%) 2-[ethanesulfonyl-(6-fluoro-2,2-dimethylchroman-4-yl)amino]-N-(5-methylisoxazol-3-yl)acetamide are obtained from 380 mg (1.0 mmol) of [ethylsulfonyl-(6-fluoro-2,2-dimethylchroman-4-yl)amino]acetyl chloride and 98 mg (1 mmol) of 3-amino-5-methylisoxazole as a solid (m.p. 183° C.).

EXAMPLE 54
2-[Ethanesulfonyl-(6-fluoro-2,2-dimethylchroman-4-yl)amino]-N-(1H-[1,2,4]triazol-3-yl)acetamide

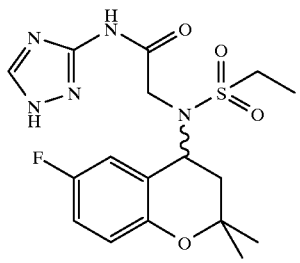

Analogously to Example 22, 610 mg (60%) of 2-[ethanesulfonyl-(6-fluoro-2,2-dimethylchroman-4-yl)amino]-N-(1H-[1,2,4]triazol-3-yl)acetamide are obtained from 1.1 g (3.0 mmol) of [ethylsulfonyl-(6-fluoro-2,2-dimethylchroman-4-yl)amino]acetyl chloride and 210 mg (2.5 mmol) of 3-aminotriazole as an oil.

EXAMPLE 55
2-[Ethanesulfonyl-(6-fluoro-2,2-dimethylchroman-4-yl)amino]-N-[2-(4-methoxy-3-sulfamoylphenyl)ethyl]acetamide

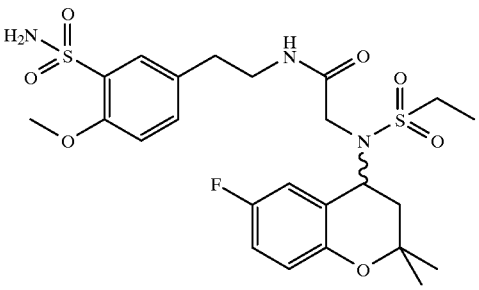

Analogously to Example 22, 140 mg (25%) of 2-[ethanesulfonyl-(6-fluoro-2,2-dimethylchroman-4-yl)amino]-N-[2-(4-methoxy-3-sulfamoylphenyl)-ethyl]acetamide are obtained from 380 mg (1.0 mmol) of [ethylsulfonyl-(6-fluoro-2,2-dimethylchroman-4-yl)amino]acetyl chloride and 270 mg (1.0 mmol) of 5-(2-aminoethyl)-2-methoxybenzenesulfonamide hydrochloride as an oil.

EXAMPLE 56
N-(6-Butoxy-2,2-dimethylchroman-4-yl)-N-(2-guanidino-2-oxoethyl)methanesulfonamide

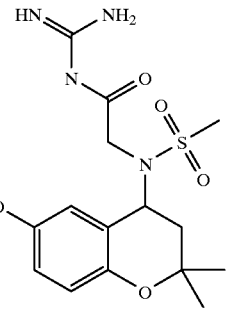

a) [(6-Butoxy-2,2-dimethylchroman-4-yl)methanesulfonylamino]acetic acid By hydrolysis of ethyl [(6-butoxy-2,2-dimethylchroman-4-yl)methanesulfonylamino]acetate (Example 41e), the corresponding acid was obtained; m.p. 108–110° C.

b) A suspension of 0.77 g (2 mmol) of [(6-butoxy-2,2-dimethylchroman-4-yl)methanesulfonylamino]acetic acid and 0.39 g (2.4 mmol) of CDI in 10 ml of THF was stirred overnight at RT. After addition of 0.59 g (10 mmol) of guanidine, the reaction mixture was additionally stirred for 3 h and then concentrated in vacuo. By stirrring the residue with 50 ml of water overnight, a crystalline product was obtained which was filtered off with suction and dried in vacuo. 0.8 g of N-(6-butoxy-2,2-dimethylchroman-4-yl)-N-(2-guanidino-2-oxoethyl)methanesulfonamide was obtained; m.p. 112–114° C.

EXAMPLE 57
N-(6-Fluoro-2,2-dimethylchroman-4-yl)-N-(2-guanidino-2-oxoethyl)ethanesulfonamide

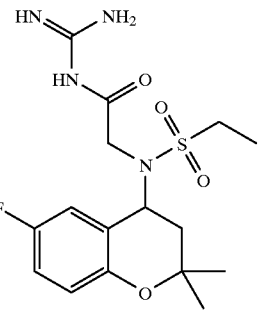

Analogously to Example 56, 310 mg (91%) of N-(6-fluoro-2,2-dimethylchroman-4-yl)-N-(2-guanidino-2-oxoethyl)ethanesulfonamide were obtained from the corresponding acid (Example 7b) as a solid (m.p. 192° C.).

EXAMPLE 58
2-[(6-Chloro-3-hydroxy-2,2-dimethylchroman-4-yl)methanesulfonylamino]-N-phenethylacetamide

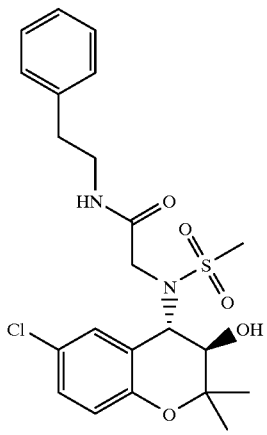

a) N-(6-Chloro-3-hydroxy-2,2-dimethylchroman-4-yl)-methanesulfonamide A solution of 2.94 g (31 mmol) of methanesulfonamide in 12 ml of DMSO was treated with 0.71 g (24 mmol) of 80 percent sodium hydride and stirred at RT for 1 h. 5.0 g (24 mmol) of 6-chloro-2,2-dimethyl-3,4-epoxychroman (J. Med. Chem. 26, 1983,1582) were then added and the mixture was heated to 60° C. for 20 h. The batch was treated with 50 ml of water, stirred for 1 h, the product which was deposited was filtered off with suction and 5.9 g of N-(6-chloro-3-hydroxy-2,2-dimethylchroman-4-yl)methanesulfonamide were obtained; m.p. 198–202° C.

b) Methyl [(6-chloro-3-hydroxy-2,2-dimethylchroman-4-yl)methanesulfonylamino]acetate A solution of 3.0 g (10 mmol) of N-(6-chloro-3-hydroxy-2,2-dimethylchroman-4-yl)methanesulfonamide was added dropwise to a solution of 0.33 g (11.3 mmol) of 80 percent sodium hydride in 25 ml of DMF and the mixture was additionally stirred at RT for 1 h. 1.53 g (10 mmol) of methyl bromoacetate were then added, the mixture was stirred overnight at RT and then the solvent was stripped off in vacuo. The residue was taken up in EA and water, the organic phase was concentrated and the product was purified by chromatography on silica gel using cyclohexane/ethyl acetate 9:1. 2.0 g of methyl [(6-chloro-3-hydroxy-2,2-dimethylchroman-4-yl)-methanesulfonylamino]acetate were obtained; m.p. 148–150° C.

c) [(6-Chloro-3-hydroxy-2,2-dimethylchroman-4-yl)methanesulfonylamino]-acetic acid By hydrolysis of the above methyl ester with KOH in methanol/water at RT overnight, the corresponding acid was obtained; m.p. 163–167° C.

d) A solution of 0.5 g (1.37 mmol) of [(6-chloro-3-hydroxy-2,2-dimethylchroman-4-yl)methanesulfonylamino]acetic acid and 0.27 g (1.65 mmol) of CDI in 7 ml of THF was stirred at RT for 3 h. 0.33 g (2.75 mmol) of phenethylamine was then added and the reaction mixture was stirred overnight. After stripping off the solvent, the residue was taken up in EA and washed with dil. hydrochloric acid and water. After purification through a short chromatography column, 0.56 g of 2-[(6-chloro-3-hydroxy-2,2-dimethylchroman-4-yl)methanesulfonylamino]-N-phenethylacetamide was obtained; m.p. 168–170° C.

EXAMPLE 59

2-[Ethanesulfonyl-(6-fluoro-2,2-dimethyl-chroman-4-yl)-amino]-N-[2-(4-fluoro-phenyl)-ethyl]-acetamide

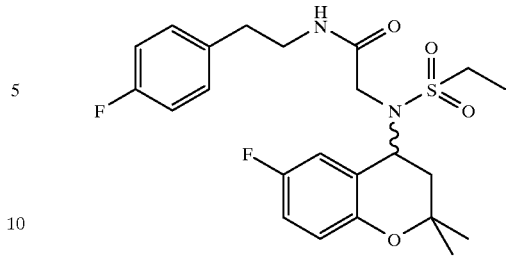

Analogously to Example 7, 420 mg of the substance were obtained.

EXAMPLE 60

2-[(6-Chloro-3-hydroxy-2,2-dimethyl-chroman-4-yl)-methanesulfonyl-amino]-N,N-dimethyl-acetamide

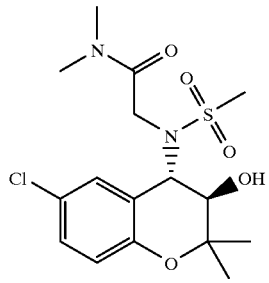

Analogously to Example 58, 150 mg of the substance having a melting point of 263° C. were obtained.

EXAMPLE 61

N-(1H-Benzoimidazol-2-yl)-2-[ethanesulfonyl-(6-fluoro-2,2-dimethyl-chroman-4-yl)-amino]-acetamide

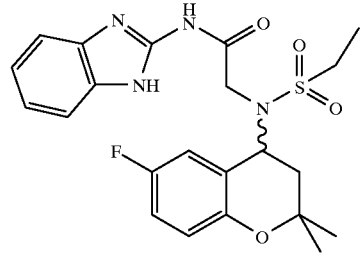

Analogously to Example 7, 340 mg of the substance having a melting point of 127–133° C. were obtained.

EXAMPLE 62

N-[2-(Benzyl-methyl-amino)-ethyl]-2-[ethanesulfonyl-(6-fluoro-2,2-dimethyl-chroman-4-yl)-amino]-acetamide

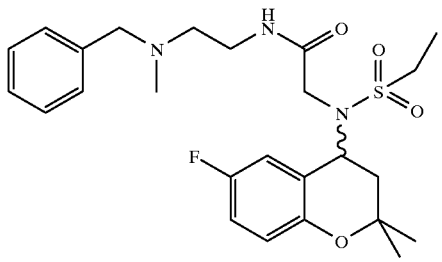

The compound was obtained analogously to Example 7 from N-Benzyl-N-methyl-ethane-1,2-diamine (Arzneim. Forsch. 25, 1975, 1853) and the corresponding acid (example 7c). After purification by chromatography 280 mg were obtained as an oil.

PHARMACOLOGICAL INVESTIGATIONS $I_{sK}$ channels from man, rat or guinea-pigs were expressed in *Xenopus oocytes*. To do this, oocytes were first isolated from Xenopus laevis and defolliculated. $I_{sK}$-encoding RNA synthesized in vitro was then injected into these oocytes. After 2–8 days of $I_{sK}$ protein expression, $I_{sK}$ currents were measured in the oocytes using the two-microelectrode voltage-clamp technique. As a rule, the $I_{sK}$ channels were in this case activated to –10 mV using voltage jumps lasting 15 s. The bath was irrigated with a solution of the following composition: NaCl 96 mM, KCl 2 mM, $CaCl_2$ 1.8 mM, $MgCl_2$ 1 mM, HEPES 5 mM (titrated with NaOH to pH 7.5). These experiments were carried out at room temperature. The following were employed for data acquisition and analysis: Geneclamp amplifier (Axon Instruments, Foster City, USA) and MacLab D/A converter and software (ADInstruments, Castle Hill, Australia). The substances according to the invention were tested by adding them to the bath solution in different concentrations. The effects of these substances were calculated as the percentage inhibition of the $I_{sK}$ control current, which was obtained when no substance was added to the solution. The data were then extrapolated using the Hill equation in order to determine the inhibitory concentrations $IC_{50}$ for the respective substances.

REFERENCES

A. E. Busch, H.-G. Kopp, S. Waldegger, I. Samarzija, H. S üβbrich, G. Raber, K. Kunzelmann, J. P. Ruppersberg and F. Lang; "Inhibition of both exogenously expressed $I_{sK}$ and endogenous K⁺ channels in *Xenopus oocytes* by isosorbide dinitrate"; J. Physiol. 491 (1995), 735–741;

T. Takumi, H. Ohkubo and S. Nakanishi; "Cloning of a membrane protein that induces a slow voltage-gated potassium current"; Science 242 (1989), 1042–1045;

M. D. Varnum, A. E. Busch, C. T. Bond, J. Maylie and J. P. Adelman; "The minK channel underlies the cardiac potassium current and mediates species-specific responses to protein kinase"; C. Proc. Natl. Acad. Sci. USA 90 (1993), 11528–11532.

For the compounds according to the invention, the following $IC_{50}$ values were determined in the manner described using human $I_{sK}$ protein:

| Compound | $IC_{50}$ [μM] |
|---|---|
| Example 4 | 1.0 |
| Example 9 | 1.6 |
| Example 10 | 0.79 |
| Example 14 | 0.18 |
| Example 17 | <<1 |
| Example 21 | 0.046 |
| Example 22 | 0.67 |
| Example 23 | 0.55 |
| Example 24 | 1.0 |
| Example 25 | 0.45 |
| Example 27 | 2.1 |
| Example 28 | 0.47 |
| Example 29 | <1 |
| Example 31 | 0.28 |
| Example 32 | 0.25 |
| Example 34 | ~0.7 |
| Example 38 | 1.42 |
| Example 39 | 0.31 |
| Example 40 | 0.35 |
| Example 42 | 0.34 |
| Example 43 | 7.8 |
| Example 45 | 0.45 |
| Example 47 | 0.75 |
| Example 49 | 0.083 |
| Example 54 | 0.83 |
| Example 56 | 3.4 |
| Example 58 | 0.5 |
| Example 59 | <0.1 |
| Example 61 | <1 |
| Example 62 | <1 |

We claim:
1. A compound of the formula I,

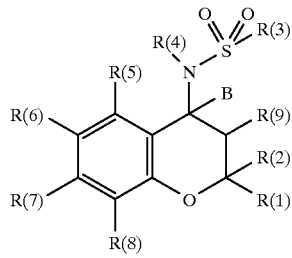

in which:
R(1) and R(2)
independently of one another are hydrogen, $CF_3$, $C_2F_5$, $C_3F_7$, alkyl having 1, 2, 3, 4, 5, or 6 carbon atoms, or phenyl,
where the phenyl is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, and methylsulfonylamino; or R(1) and R(2) together are an alkylene chain having 2, 3, 4, 5, 6, 7, 8, 9, or 10 carbon atoms;

R(3) is R(10)—$C_nH_{2n}$—NR(11)— or R(10)—$C_nH_{2n}$—, where one $CH_2$ group in the groups $C_nH_{2n}$ can be replaced by —O—, —CO—, —S—, —SO—, —$SO_2$—, or —NR(12a)—;

R(12a) is hydrogen, methyl, or ethyl;
R(10) is hydrogen, methyl, cycloalkyl having 3, 4, 5, 6, 7, or 8 carbon atoms, $CF_3$, $C_2F_5$, or $C_3F_7$;
n is zero, 1, 2, 3, 4, 5, 6, 7, 8, 9, or 10;
R(11) is hydrogen or alkyl having 1, 2, 3, 4, 5, or 6 carbon atoms; or R(10) and R(11) together are a bond, provided n is not smaller than 3;

R(4) is R(13)—$C_rH_{2r}$—Z—$C_qH_{2q}$—;

q is 0, 1, 2, 3, 4, 5, 6, 7, or 8;

r is 0, 1, 2, 3, 4, 5, 6, 7, or 8;

Z is —CO—NR(14)—,
—OCO—NR(14)—,
—O—$C_xH_{2x}$—O—,
—O—$C_xH_{2x}$—NR(14)—,
—O—$C_xH_{2x}$—CO—O,
—CO—O—$C_xH_{2x}$—O— or
—CO—O—$C_xH_{2x}$—NR(14)—, where Z may be linked in the forward or reverse directions, x is 2, 3, or 4;

R(14) is hydrogen, alkyl having 1, 2, or 3 carbon atoms,
—$C_yH_{2y}$—OR(12b), —$C_yH_{2y}$—NR(12b)$_2$;

R(12b) is hydrogen, methyl, or ethyl;

y is 2 or 3;

R(13) is H, $CF_3$, $C_2F_5$, $C_3F_7$, cycloalkyl having 3, 4, 5, 6, 7, or 8 carbon atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;

R(15) and R(16)
independently of one another are hydrogen, alkyl having 1, 2, 3, or 4 carbon atoms or —$C_zH_{2z}$-phenyl,
z is zero, 1, or 2;
where phenyl is unsubstituted or substituted by 1 or 2 substituents which are F, Cl, Br, $CF_3$, $NO_2$, CN, OH, methyl, ethyl, methoxy, dimethylamino, sulfamoyl, methylsulfonyl, aminosulfonyl, and methylsulfonylamino; or R(15) and R(16)
together are a chain of 4 or 5 methylene groups, of which one $CH_2$ group can be replaced by —O—, —S—, —NH—, —N($CH_3$)—, or —N(benzyl)—;

R(17) is hydrogen or alkyl having 1, 2, or 3 carbon atoms;

R(5), R(6), R(7), and R(8)
independently of one another are hydrogen, F, Cl, Br, I, alkyl having 1, 2, 3, 4, or 5 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —Y—$C_sH_{2s}$—R(18), or phenyl,
where phenyl is unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;

Y is —O—, —CO—, —CO—O—, —O—CO—, —S—, —SO—, —$SO_2$—, —$SO_2$—O—, —$SO_2$NR(10c), —NR(10c)—, or —CONR(10c)—;

R(10c) is hydrogen or alkyl having 1, 2, or 3 carbon atoms;

s is zero, 1, 2, 3, 4, 5, or 6;

R(18) is hydrogen, $CF_3$, $C_2F_5$, $C_3F_7$, cycloalkyl having 3, 4, 5, 6, 7, or 8 carbon atoms, —COOR (21), 1-piperidyl, 1-pyrrolidinyl, 4-morpholinyl, 4-methylpiperazin-1-yl, pyridyl, thienyl, imidazolyl, quinolyl, isoquinolyl, or phenyl, where pyridyl, thienyl, imidazolyl, quinolyl, isoquinolyl, and phenyl are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;

R(21) is hydrogen or alkyl having 1, 2, or 3 carbon atoms;

R(9) is hydrogen, OR(10d), or OCOR(10d);

R(10d) is hydrogen or alkyl having 1, 2, or 3 carbon atoms;

B is hydrogen; or

R(9) and B
together are a bond;

or a physiologically tolerable salt thereof.

2. A compound or a salt of the formula I as claimed in claim 1, in which:

R(1) and R(2)
independently of one another are hydrogen, $CF_3$ or alkyl having 1, 2, 3, 4, 5, or 6 carbon atoms; or R(1) and R(2) together are an alkylene chain having 2, 3, 4, 5, or 6 carbon atoms;

R(3) is R(10)—$C_nH_{2n}$—;

R(10) is methyl, $CF_3$ or $C_2F_5$;

n is zero, 1, or 2;

R(4) is R(13)—$C_rH_{2r}$—Z—$C_qH_{2q}$—;

q is 1, 2, 3, 4, 5, 6, 7, or 8;

r is 0, 1, 2, 3, 4, 5, 6, 7, or 8;

Z is —CO—NR(14)—,
—OCO—NR(14)—,
—O—$C_xH_{2x}$—O—,
—O—$C_xH_{2x}$—NR(14)—,
—O—$C_xH_{2x}$—CO—O,
—CO—O—$C_xH_{2x}$—O— or
—CO—O—$C_xH_{2x}$—NR(14)—, where Z may be linked in the forward or reverse directions;

x is 2, 3, or 4;

R(14) is hydrogen, alkyl having 1, 2, or 3 carbon atoms, $C_yH_{2y}$—OR(12b), —$C_yH_{2y}$—NR(12b)$_2$;

R(12b) is hydrogen, methyl, or ethyl;

y is 2 or 3;

R(13) is H, $CF_3$, $C_2F_5$, $C_3F_7$, cycloalkyl having 3, 4, 5, 6, 7, or 8 carbon atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is
unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino;

R(15) and R(16)
independently of one another are hydrogen, alkyl having 1, 2, 3, or 4 carbon atoms or —$C_zH_{2z}$-phenyl,
z is zero, 1, or 2;
where phenyl is unsubstituted or substituted by 1 or 2 substituents which are F, Cl, Br, $CF_3$, $NO_2$, CN, OH, methyl, ethyl, methoxy, dimethylamino, sulfamoyl, methylsulfonyl, aminosulfonyl, and methylsulfonylamino; or R(15) and R(16)
  together are a chain of 4 or 5 methylene groups, of which one $CH_2$ group can be replaced by —O—, —S—, —NH—, —N($CH_3$)—, or —N(benzyl)—;
R(17) is hydrogen or alkyl having 1, 2, or 3 carbon atoms;
R(5), R(6), R(7), and R(8)
  independently of one another are hydrogen, F, Cl, Br, I, alkyl having 1, 2, 3, 4, or 5 carbon atoms, cycloalkyl having 3, 4, 5, 6, or 7 carbon atoms, —CN, —$CF_3$, —$C_2F_5$, —$C_3F_7$, —$NO_2$, —Y—$C_sH_{2s}$—R(18), or phenyl, when phenyl is unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
  Y is —O—, —CO—, —CO—O—, —O—CO—, —S—, —SO—, —$SO_2$—, —$SO_2$—O—, —$SO_2$NR(10c), —NR(10c)—, or —CONR(10c)—;
    R(10c) is hydrogen or alkyl having 1, 2, or 3 carbon atoms;
  s is zero, 1, 2, 3, 4, 5, or 6;
  R(18) is hydrogen, $CF_3$, $C_2F_5$, $C_3F_7$, cycloalkyl having 3, 4, 5, 6, or 7 carbon atoms, —COOR(21), 1-piperidyl, 1-pyrrolidinyl, 4-morpholinyl, 4-methylpiperazin-1-yl, pyridyl, imidazolyl, or phenyl, where pyridyl, imidazolyl, and phenyl are unsubstituted or substituted by 1 or 2 substituents which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
    R(21) is hydrogen or alkyl having 1, 2, or 3 carbon atoms;
R(9) is hydrogen or OR(10d);
R(10d) is hydrogen or methyl;
B is hydrogen; or
R(9) and B
  together are a bond.

3. A compound or a salt of the formula I as claimed in claim 1, in which:
R(1) and R(2) independently of one another are hydrogen, $CF_3$, or alkyl having 1, 2, or 3 carbon atoms; or
R(1) and R(2) together are an alkylene chain having 2, 3, 4, or 5 carbon atoms;
R(3) is R(10)—$C_nH_{2n}$—;
  R(10) is methyl, $CF_3$, or $C_2F_5$;
  n is zero, 1, or 2;
R(4) is R(13)—$C_rH_{2r}$—Z—$C_qH_{2q}$—;
  q is 1, 2, 3, or 4;
  r is 0, 1, 2, or 3;
  Z is —CO—NR(14)—,
    —OCO—NR(14)—,
    —O—$C_xH_{2x}$—O—,
    —O—$C_xH_{2x}$—NR(14)—,
    —O—$C_xH_{2x}$—CO—O,
    —CO—O—$C_xH_{2x}$—O— or
    —CO—O—$C_xH_{2x}$—NR(14)—,
    where Z may be linked in the forward or reverse directions;
    x is 2 or 3;
R(14) is hydrogen, alkyl having 1 or 2 carbon atoms;
R(13) is $CH_3$, $CF_3$, $C_2F_5$, cycloalkyl having 3, 4, 5, 6, or 7 carbon atoms, —NR(15)R(16), —OR(17), —COOR(17), phenyl, or an N-containing heterocycle having 1, 2, 3, 4, 5, 6, 7, 8, or 9 carbon atoms, where phenyl and the N-containing heterocycle is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino; R(15) and R(16)
    independently of one another are hydrogen or alkyl having 1, 2, 3, or 4 carbon atoms; or
  R(15) and R(16)
    together are a chain of 4 or 5 methylene groups, of which one $CH_2$ group can be replaced by —O—, —S—, —NH—, —N($CH_3$)—, or —N(benzyl)—;
  R(17) is hydrogen or alkyl having 1 or 2 carbon atoms;
R(5) and R(6)
  independently of one another are hydrogen, F, Cl, Br, alkyl having 1, 2, 3, 4, or 5 carbon atoms, cycloalkyl having 3, 4, 5, 6, or 7 carbon atoms, —CN, —$CF_3$, —$C_2F_5$, —$NO_2$, —Y—$C_sH_{2s}$—R(18), or phenyl, where phenyl is unsubstituted or substituted by 1 or 2 substituents, which are F, Cl, Br, I, $CF_3$, $NO_2$, CN, $NH_2$, OH, methyl, ethyl, methoxy, dimethylamino, sulfamoyl, methylsulfonyl, and methylsulfonylamino;
  Y is —O—, —CO—, —$SO_2$—, or —CONR(10c)—;
    R(10c) is hydrogen or alkyl having 1 or 2 carbon atoms;
  s is zero, 1, 2, 3, 4, 5, or 6;
  R(18) is hydrogen, $CF_3$, $C_2F_5$, cycloalkyl having 3, 4, 5, 6, or 7 carbon atoms, 1-piperidyl, 1-pyrrolidinyl, 4-morpholinyl, 4-methylpiperazin-1-yl, pyridyl, imidazolyl, or phenyl, where pyridyl, imidazolyl, and phenyl are unsubstituted or substituted by 1 or 2 substituents which are F, Cl, Br, $CF_3$, $NO_2$, CN, $NH_2$, OH, methyl, ethyl, methoxy, dimethylamino, sulfamoyl, methylsulfonyl, and methylsulfonylamino;
R(7) and R(8)
  are hydrogen;
R(9) is hydrogen or OR(10d);
  R(10d) is hydrogen or methyl;
B is hydrogen; or
R(9) and B
  together form a bond.

4. A compound or a salt of the formula I as claimed in claim 1, in which:
R(1) and R(2) are methyl;
R(3) is methyl or ethyl;
R(4) is R(13)—$C_rH_{2r}$—Z—$C_qH_{2q}$—;
  q is 1, 2, 3, or 4;
  r is 0, 1, 2, or 3;
  Z is —CO—NR(14)—,
    —OCO—NR(14)—,
    —O—$C_xH_{2x}$—NR(14)— or
    —CO—O—$C_xH_{2x}$—NR(14)—;
    x is 2 or 3;
  R(14) is hydrogen or methyl;
  R(13) is $CH_3$, $CF_3$, —OR(17), —COOR(17), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —CF$_3$, —Y—C$_s$H$_{2s}$—R(18), or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
Y is —O—, —CO—, or —CONR(10c)—;
R(10c) is hydrogen or methyl;
s is 1, 2, 3, 4, or 5;
R(18) is hydrogen, CF$_3$, or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, and methylsulfonylamino;

R(7) and R(8) are hydrogen;
R(9) is hydrogen;
B is hydrogen.

5. A compound or a salt of the formula I as claimed in claim 1, in which:
R(1) and R(2) are methyl;
R(3) is methyl or ethyl;
R(4) is R(13)—C$_r$H$_{2r}$—Z—C$_q$H$_{2q}$—;
q is 1, 2, 3, or 4;
r is 0, 1, 2, or 3;
Z is —CO—NR(14)—,
—OCO—NR(14)—,
—O—C$_x$H$_{2x}$—NR(14)— or
—CO—O—C$_x$H$_{2x}$—NR(14)—;
x is 2 or 3;
R(14) is hydrogen or methyl;
R(13) is CH$_3$, CF$_3$, —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —CF$_3$, —Y—C$_s$H$_{2s}$—R(18) or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
Y is —O—, —CO—, or —CONR(10c)—;
R(10c) is hydrogen or methyl;
s is 1, 2, 3, 4, or 5;
R(18) is hydrogen, CF$_3$, or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, and methylsulfonylamino;

R(7) and R(8) are hydrogen;
R(9) is OH;
B is hydrogen.

6. A compound or a salt of the formula I as claimed in claim 1, in which:
R(1) and R(2) are methyl;
R(3) is methyl or ethyl;
R(4) is R(13)—C$_r$H$_{2r}$—Z—C$_q$H$_{2q}$—;
q is 1, 2, 3, or 4;
r is 0, 1, 2, or 3;
Z is —CO—NR(14)—,
—OCO—NR(14)—,
—O—C$_x$H$_{2x}$—NR(14)— or
—CO—O—C$_x$H$_{2x}$—NR(14)—;
x is 2 or 3;
R(14) is hydrogen or methyl;
R(13) is CH$_3$, CF$_3$, —OR(17), —COOR(17), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, aminosulfonyl, or methylsulfonylamino;
R(17) is hydrogen or alkyl having 1 or 2 carbon atoms;

R(5) is hydrogen, alkyl having 1, 2, 3, or 4 carbon atoms, F, Cl, methoxy, or ethoxy;

R(6) is F, Cl, alkyl having 1, 2, 3, 4, or 5 carbon atoms, —CF$_3$, —Y—C$_s$H$_{2s}$—R(18) or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;
Y is —O—, —CO—, or —CONR(10c)—;
R(10c) is hydrogen or methyl;
s is 1, 2, 3, 4, or 5;
R(18) is hydrogen, CF$_3$, or phenyl,
where phenyl is unsubstituted or substituted by 1 or 2 substituents which are F, Cl, Br, CF$_3$, NO$_2$, CN, NH$_2$, OH, methyl, ethyl, methoxy, dimethylamino, sulfamoyl, methylsulfonyl, or methylsulfonylamino;

R(7) and R(8) are hydrogen;
R(9) and B together are a bond.

7. A pharmaceutical composition, comprising a compound of claim 6, and a pharmaceutical carrier.

8. A pharmaceutical composition according to claim 7 further comprising the addition of one or more pharmacologically active compounds.

9. A method for the treatment and prophylaxis of K$^+$ channel-mediated diseases in a patient in need thereof, comprising administering an effective amount of a compound of claim 1 to the patient.

10. A method for inhibiting stimulated gastric acid secretion in a patient in need thereof, comprising administering an effective amount of a compound of claim 1 to the patient.

11. A method for the treatment or prophylaxis of ulcers of the stomach or of the intestinal region in a patient in need thereof, comprising administering an effective amount of a compound of claim 1 to the patient.

12. A method for the treatment or prophylaxis of reflux esophagitis in a patient in need thereof, comprising administering an effective amount of a compound of claim 1 to the patient.

13. A method for the treatment or prophylaxis of diarrheal disorders in a patient in need thereof, comprising administering an effective amount of a compound of claim 1 to the patient.

14. A method for the treatment or prophylaxis of all types of arrythmias in a patient in need thereof, comprising administering an effective amount of a compound of claim 1 to the patient.

15. A method for the treatment or prophylaxis of all types of arrythmias according to claim 14 where the the arrythmias are atrial, ventricular, and supraventricular arrythmias.

16. A method for the treatment or prophylaxis of cardiac arrythmias which can be eliminated by action potential prolongation in a patient in need thereof, comprising administering an effective amount of a compound of claim 1 to the patient.

17. A method for the treatment or prophylaxis of atrial fibrillation or atrial flutters in a patient in need thereof, comprising administering an effective amount of a compound of claim 1 to the patient.

18. A method for the treatment or prophylaxis of reentry arrythmias in a patient in need thereof, comprising administering an effective amount of a compound of claim 1 to the patient.

19. A method for the prevention of sudden cardiac death as a result of ventricular fibrillation in a patient in need thereof, comprising administering an effective amount of a compound of claim 1 to the patient.

20. A method for the treatment of cardiac insufficiency in a patient in need thereof, comprising administering an effective amount of a compound of claim 1 to the patient.

\* \* \* \* \*